US007604956B2

(12) United States Patent
Drukier

(10) Patent No.: US 7,604,956 B2
(45) Date of Patent: Oct. 20, 2009

(54) SUPERSENSITIVE IMMUNOASSAYS

(75) Inventor: Andrzej J. Drukier, Burke, VA (US)

(73) Assignee: BioTraces, Inc., Herndon, VA (US)

( * ) Notice: Subject to any disclaimer, the term of this patent is extended or adjusted under 35 U.S.C. 154(b) by 302 days.

(21) Appl. No.: 11/065,347

(22) Filed: Feb. 25, 2005

(65) Prior Publication Data
US 2005/0272110 A1   Dec. 8, 2005

Related U.S. Application Data

(60) Provisional application No. 60/548,186, filed on Mar. 1, 2004.

(51) Int. Cl.
*G01N 33/53* (2006.01)
*G01N 33/534* (2006.01)
*G01N 33/535* (2006.01)

(52) U.S. Cl. ............ 435/7.9; 435/7.91; 435/7.92; 435/7.94; 435/7.5; 436/518; 436/524; 436/525; 436/526; 436/528; 436/531; 436/804

(58) Field of Classification Search ........ 435/7.4, 435/7.9, 7.92, 7.93, 7.94; 436/518, 524, 436/527, 804
See application file for complete search history.

(56) References Cited

U.S. PATENT DOCUMENTS

| 4,228,237 | A | * | 10/1980 | Hevey et al. ............ 435/5 |
| 4,376,110 | A | * | 3/1983 | David et al. ............ 435/5 |
| 4,931,385 | A | * | 6/1990 | Block et al. ............ 435/7.94 |
| 5,120,662 | A | * | 6/1992 | Chan et al. ............ 436/530 |

* cited by examiner

*Primary Examiner*—Christopher L Chin
(74) *Attorney, Agent, or Firm*—Davidson Berquist Jackson & Gowdey LLP

(57) ABSTRACT

An assay exhibiting improved sensitivity for achieving a factor of ten times (10×) better sensitivity than current sensitivity levels achieved by prior-art immunoassays, as exemplified by ELISA. Three main implementations are described: IA/MPD, Super-ELISA and Reverse Geometry Immunoassay, including specific panel biomarker relationships for the early detection and recognition patterns of breast and prostate cancers. More sensitive immunoassays are achieved through a better understanding of sources of biological background, and by the rejection of particular sources thereof. Supersensitive immunoassays permit measurement of blood sample biomarkers, and show distribution of low abundance proteins included relationships between cytokine non-Gaussian distributions, very large dynamic ranges and strong age dependence, and including new algorithms based on 2D correlations of studied biomarkers.

26 Claims, 11 Drawing Sheets

IA/MPD using $^{125}$I-streptavidin    Super-ELISA $^{125}$I             HRP

IA/MPD, ELISA and Super-ELISA

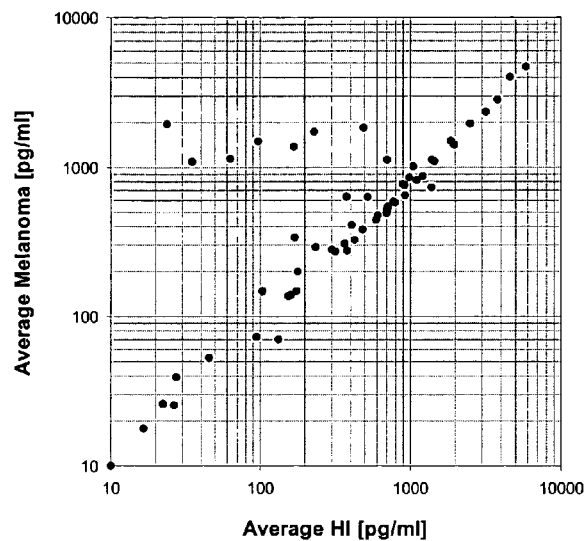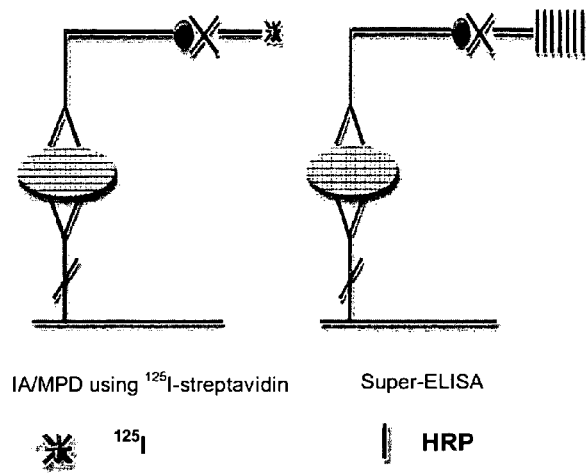
Fig. 1 : Only a few low abundance biomarkers should be considered for melanoma diagnostics
Fig. 2 : IA/MPD, ELISA and Super-ELISA
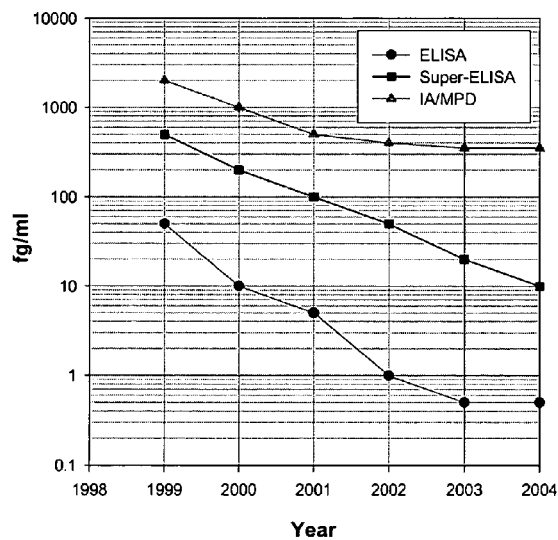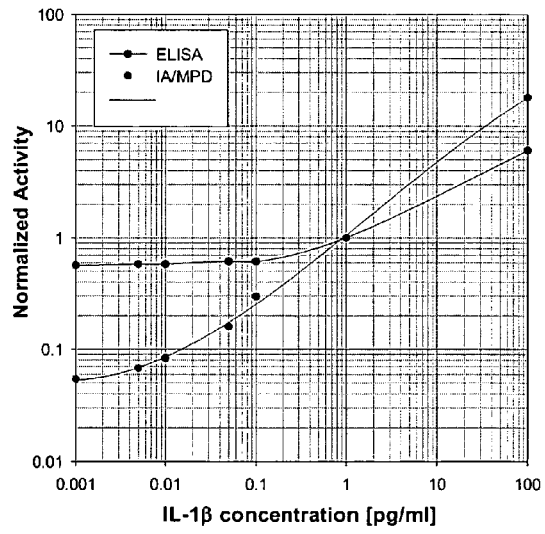
Fig. 3 : Sensitivity of IA/MPD, Super-ELISA and ELISA (1998-2004)
Fig. 4 : Comparison of sensitivity of IA/MPD and ELISA targeting IL-1β.

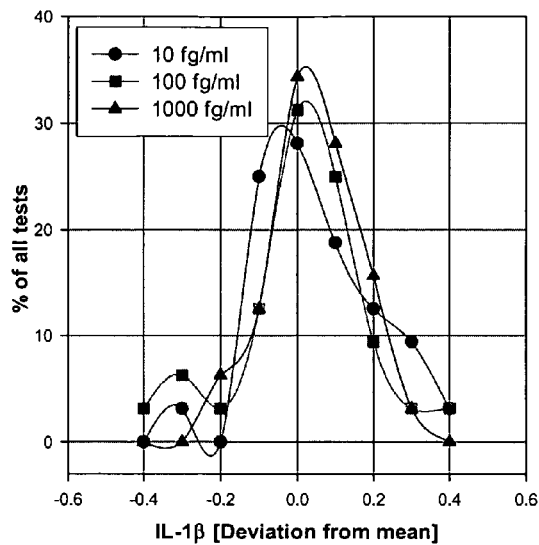
Fig. 5 : Reproducibility of IA/MPD for IL-1β.
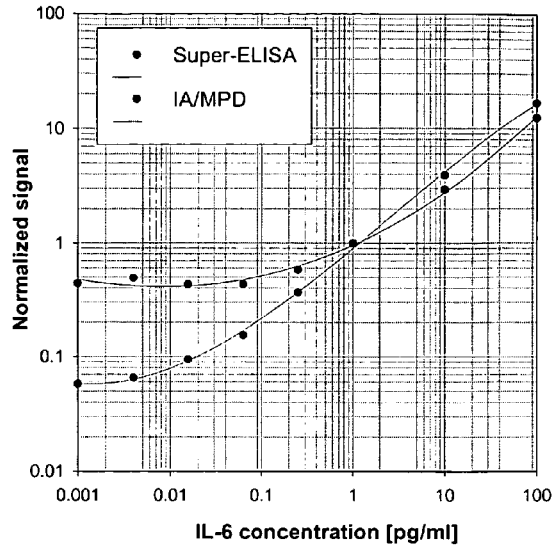
Fig. 6 : Comparison of sensitivity of IA/MPD and ELISA targeting IL-6.
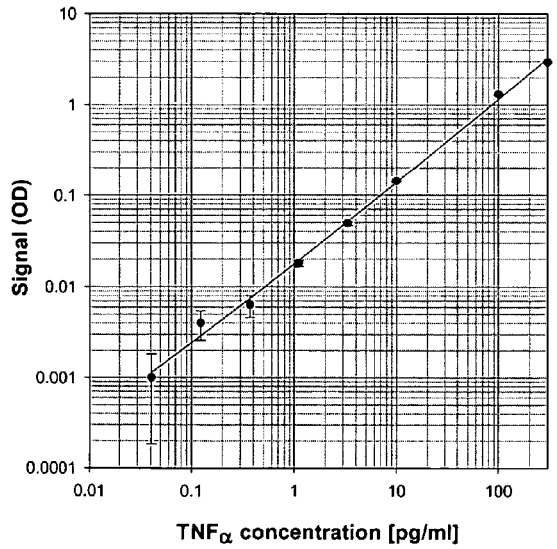
Fig. 7 : Super-ELISA for $TNF_\alpha$ using new colorimeter.
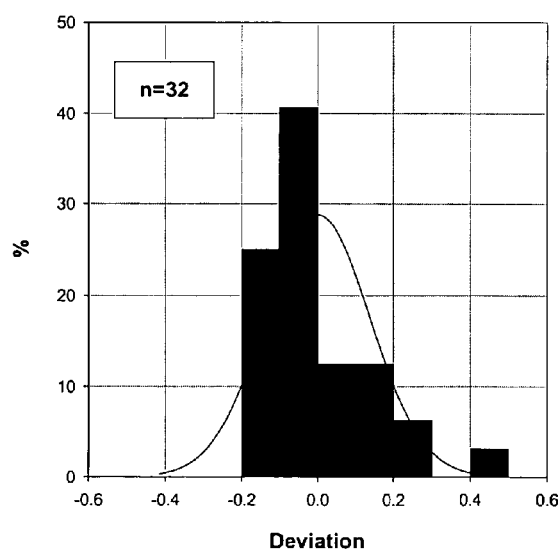
Fig. 8 : Reproducibility of Super-ELISA for Human $TNF_\alpha$ at 10 fg/ml.

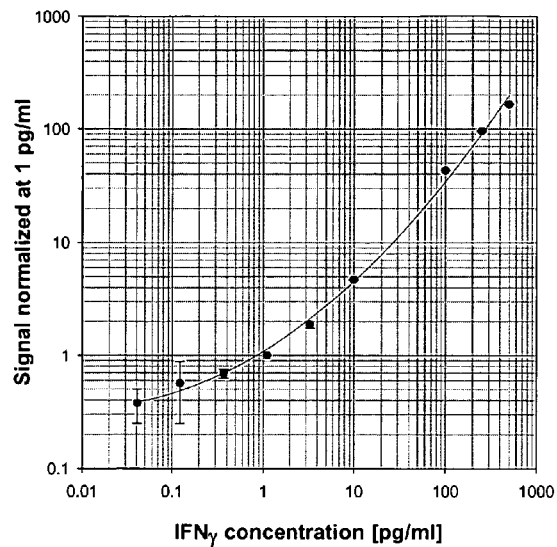
Fig. 9 : Super-ELISA for IFN$_\gamma$.
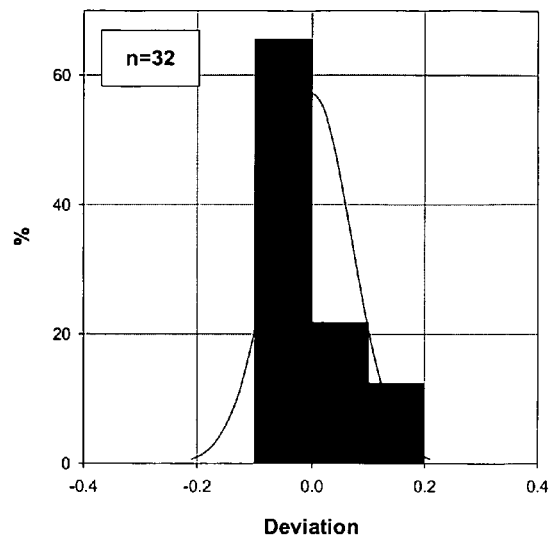
Fig. 10 : Reproducibility of ELISA for IFN$_\gamma$.
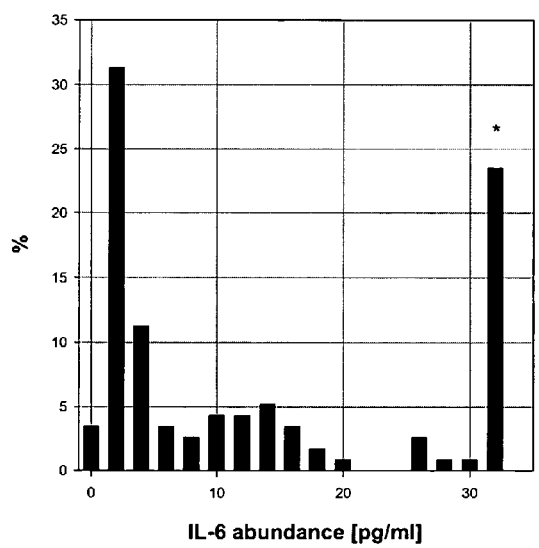
Fig. 11 : Distribution of IL-6 in 115 healthy women
* All samples with IL-6 > 30 pg/ml
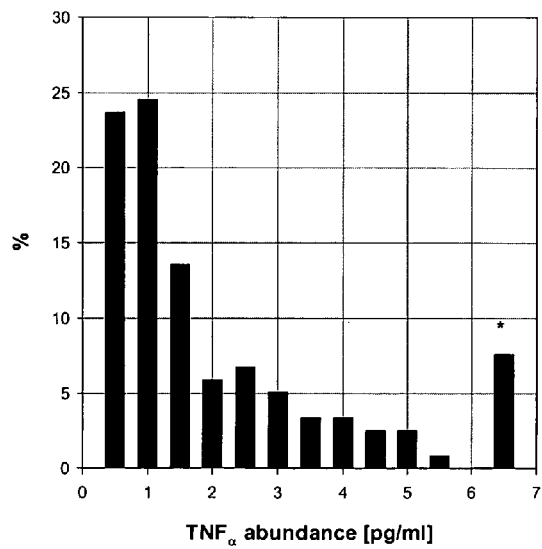
Fig. 12 : Distribution of TNF$_\alpha$ in 118 healthy women

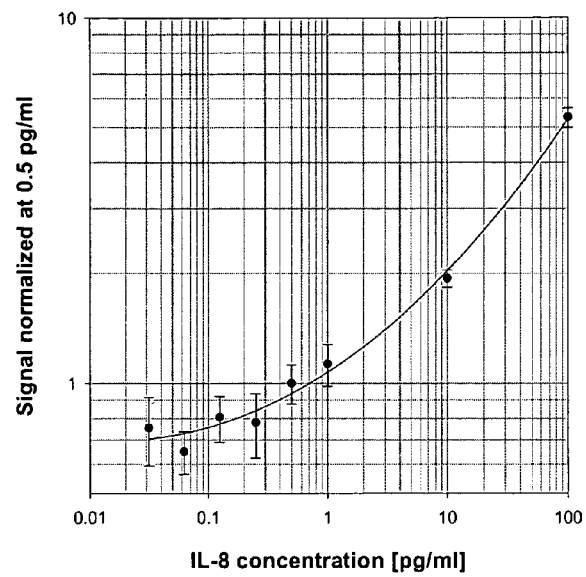
Fig. 13 : The Super-ELISA for IL-8.
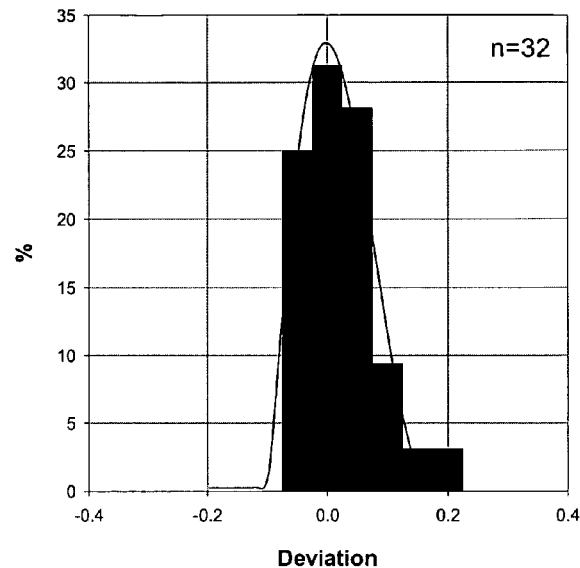
Fig. 14 : Reproducibility of Super-ELISA for IL-8 at 0.25 pg/ml.
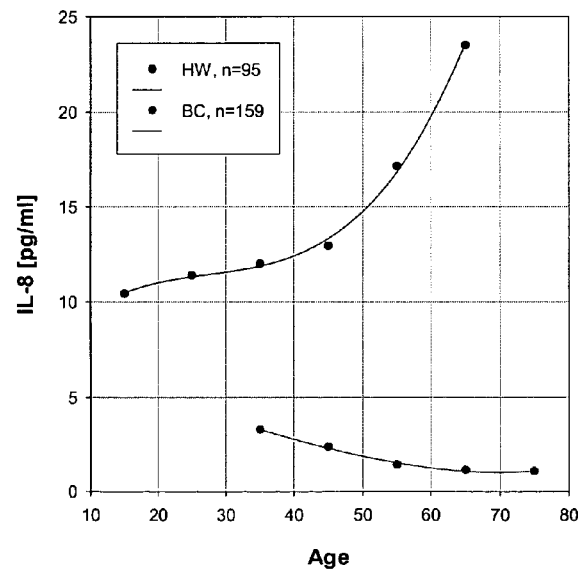
Fig. 15 : The average level of IL-8 in BC and HW cohorts
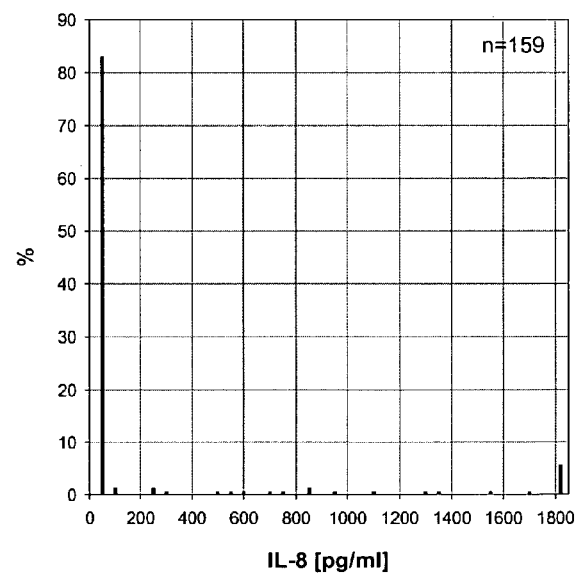
Fig. 16 : Distribution of level of IL-8 in BC cohort

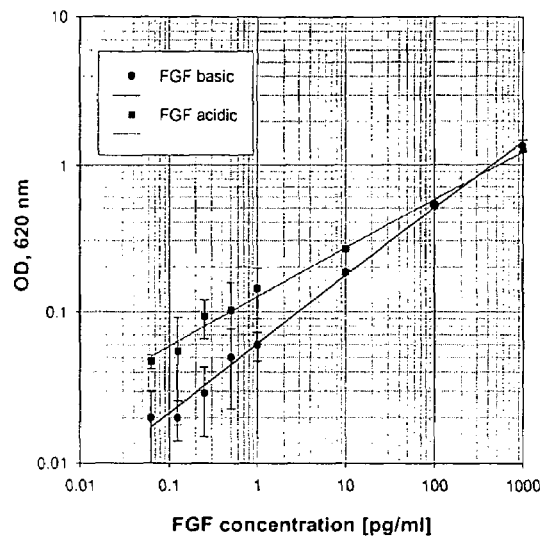
Fig. 17: Super-ELISA for FGF1$_\alpha$
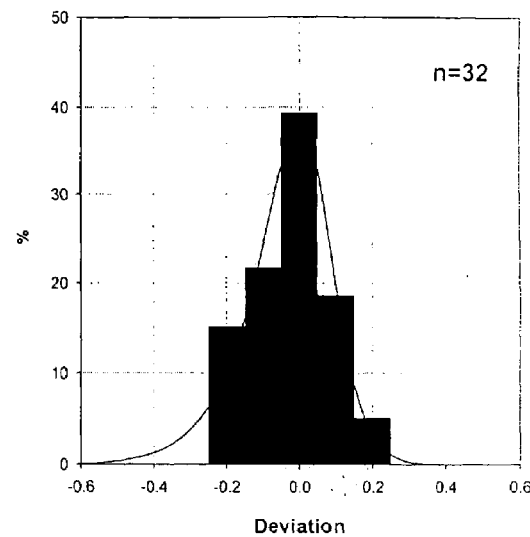
Fig. 18: Reproducibility of Super-ELISA for FGF1$_a$ at 0.1 pg/ml
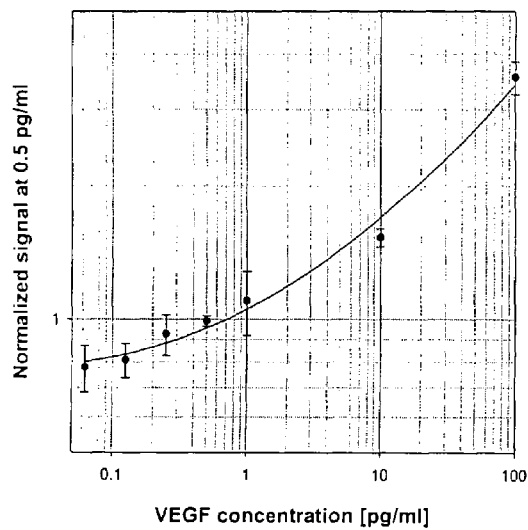
Fig. 19: Super-ELISA for VEGF
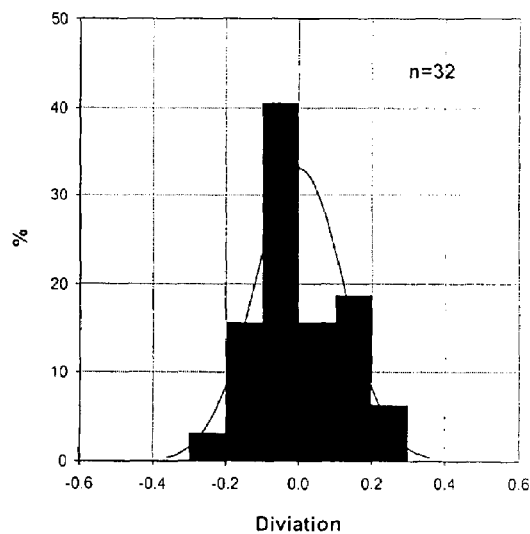
Fig. 20: Reproducibility of Super-ELISA for VEGF at 0.1 pg/ml

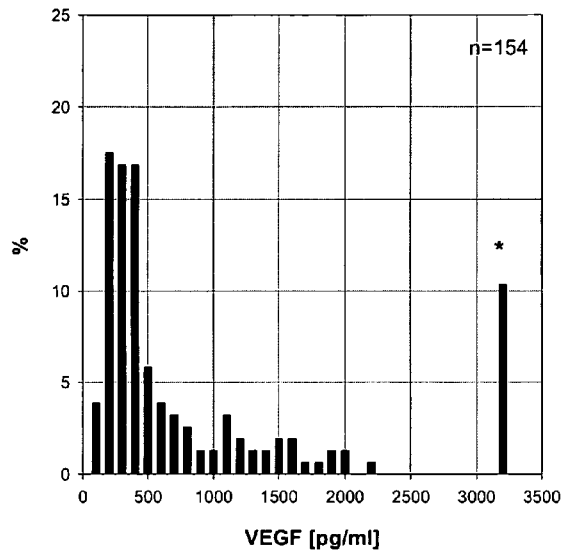
Fig. 21 : Distribution of level of VEGF in BC cohort
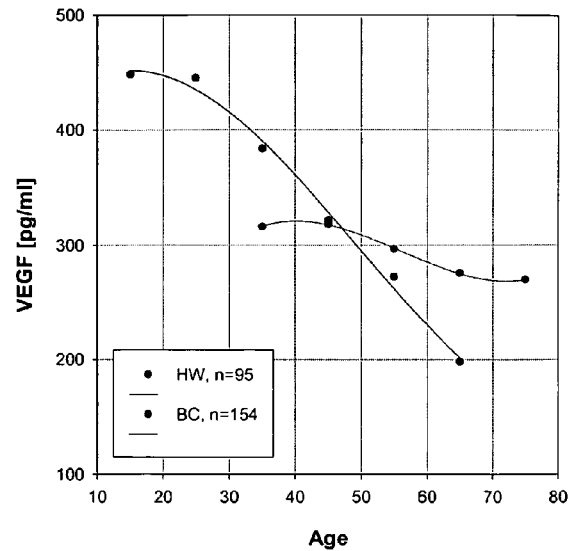
Fig. 22 : The average level of VEGF in BC and HW cohorts
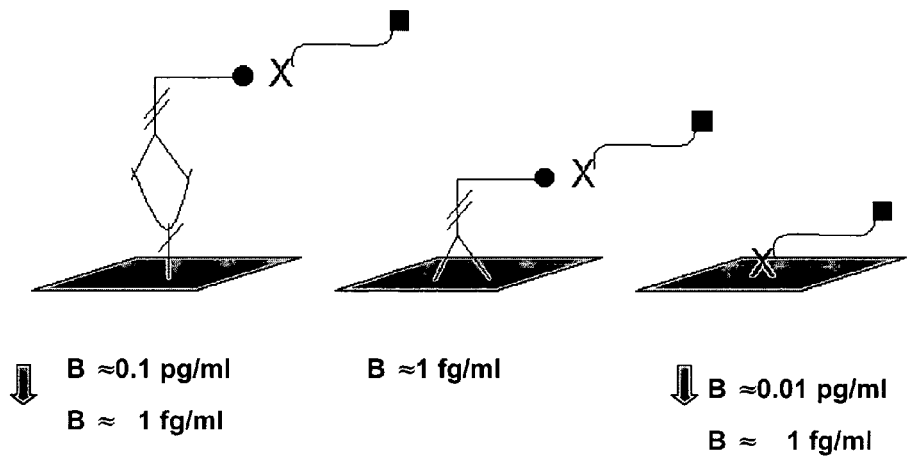
B ≈0.1 pg/ml           B ≈1 fg/ml           B ≈0.01 pg/ml
B ≈ 1 fg/ml                                  B ≈ 1 fg/ml
Fig. 23 : Biological matrix independent backgrounds.
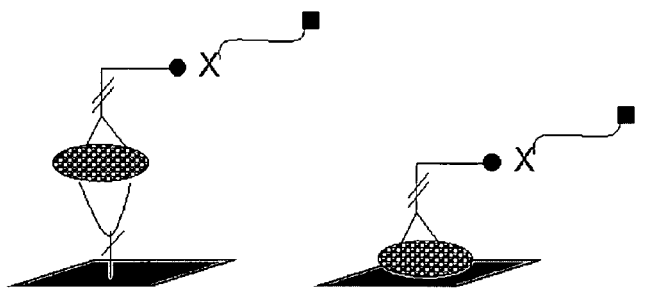
Fig. 24 : Biological matrix dependent backgrounds.

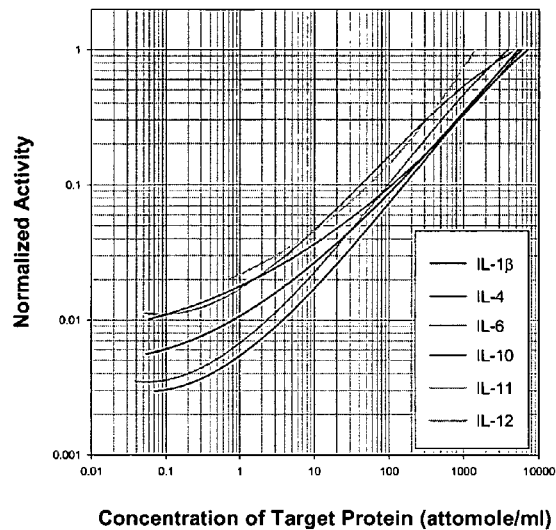
Fig. 25 : IA/MPD for interleukins: note that with different quality Abs (different slopes) we achieved the similar LOD of about 0.05-0.1 attomole/ml.
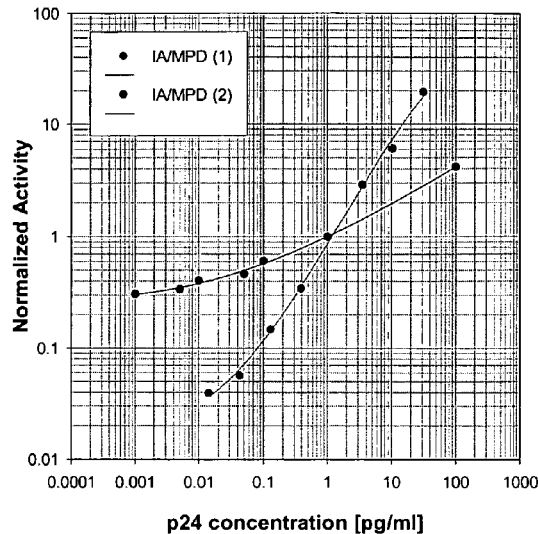
Fig. 26 : IA/MPD for p24 using the same Abs but different blocking/washing.
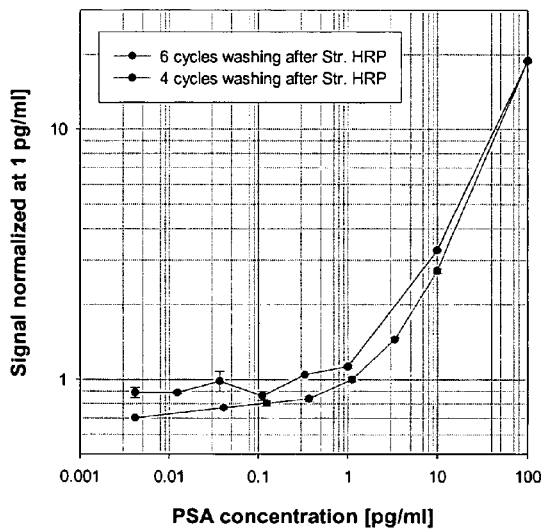
Fig. 27 : Super-ELISA for PSA; influence of of number of washes in step w 3.
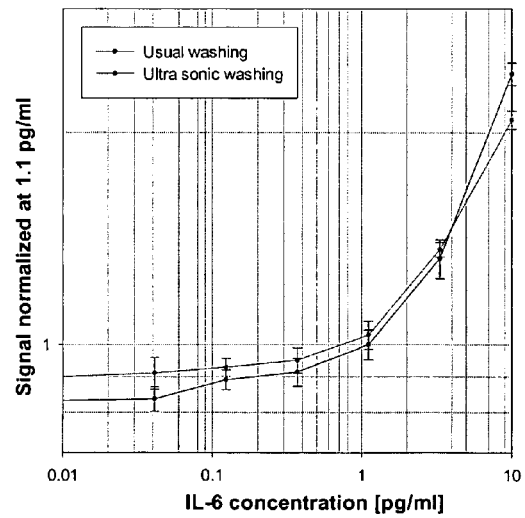
Fig. 28 : Use of ultrasound wash to improve sensitivity in 384 wells microtiter format

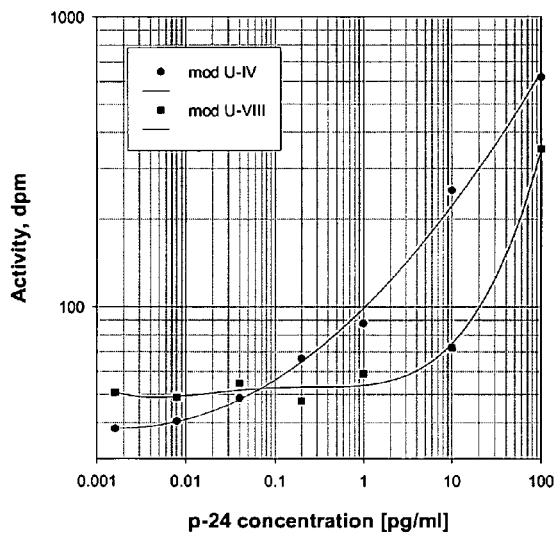
Fig.29 : IA/MPD using Mod 8 and Mod 4 assey buffers
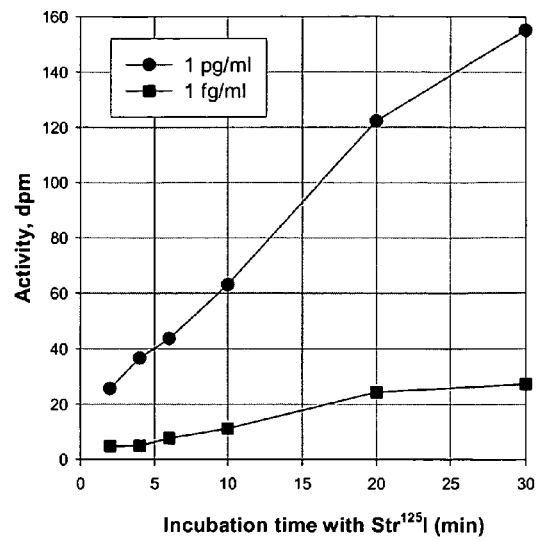
Fig. 30 : The background as function of $^{125}$I-streptavidin incubation time.
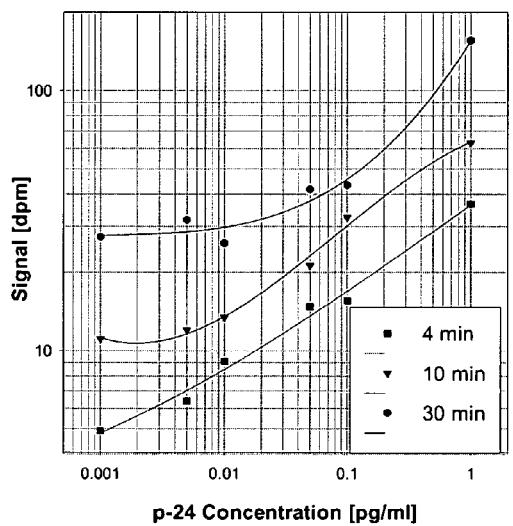
Fig. 31 : Shorter incubation time with $^{125}$I-streptavidin permits better sensitivity of IA/MPD for p24.
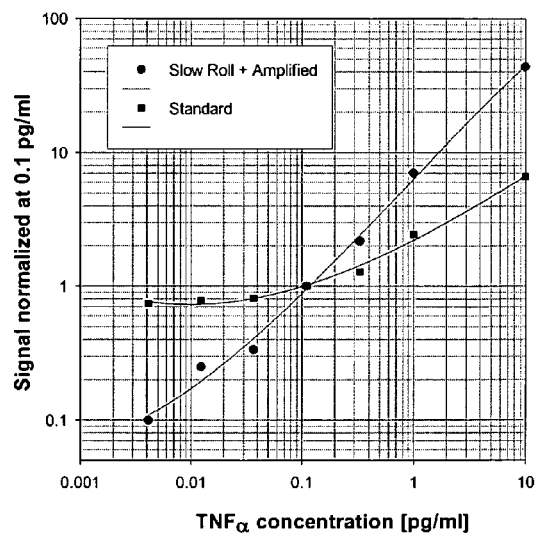
Fig. 32 : The slow roll improves sensitivity.

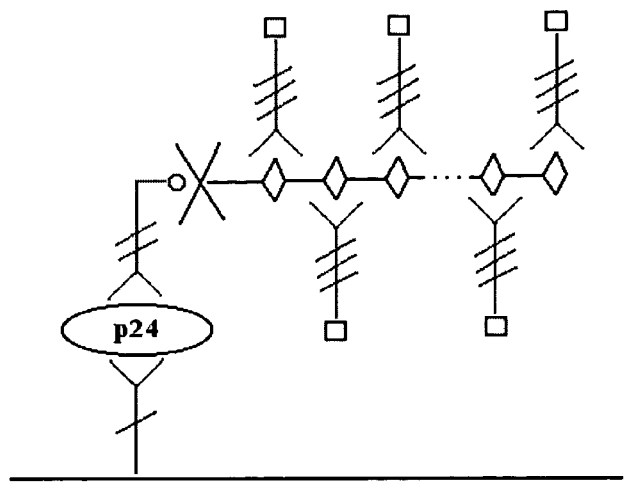
Legend
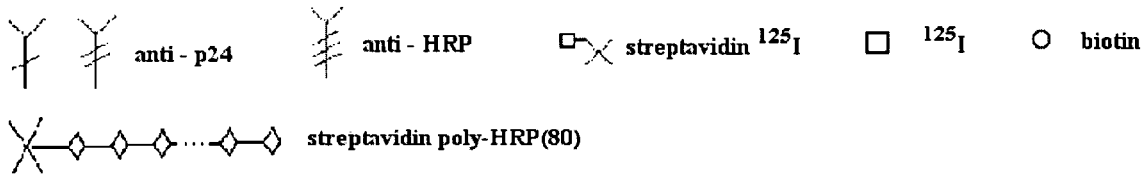
Fig. 33 : Amplified IA/MPD.
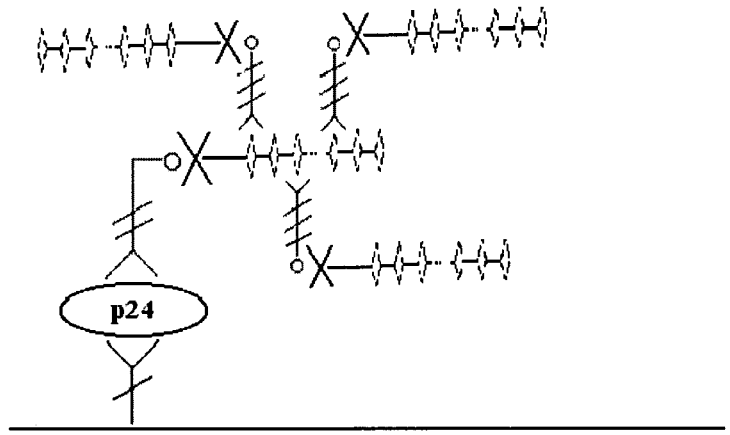
Legend
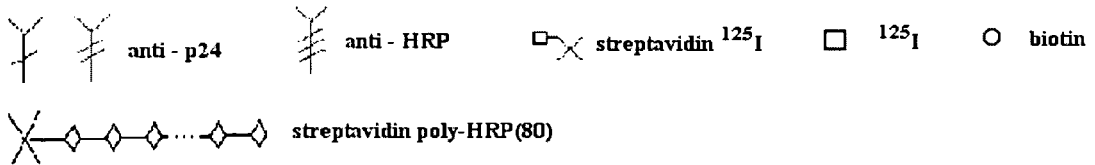
Fig. 34 : Amplified Super-ELISA.

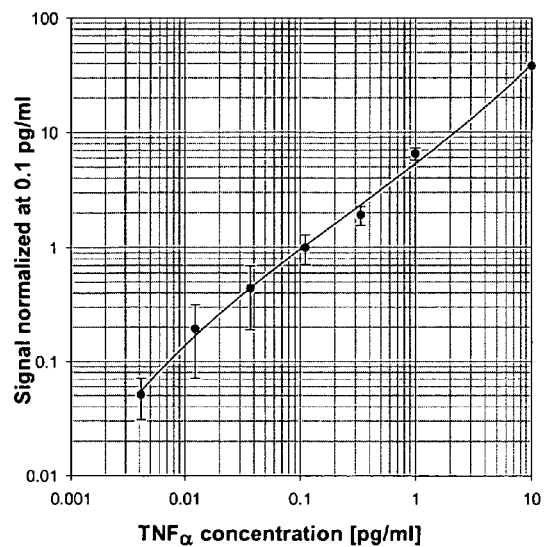
Fig. 35 : Amplified Super-ELISA for TNF$_\alpha$
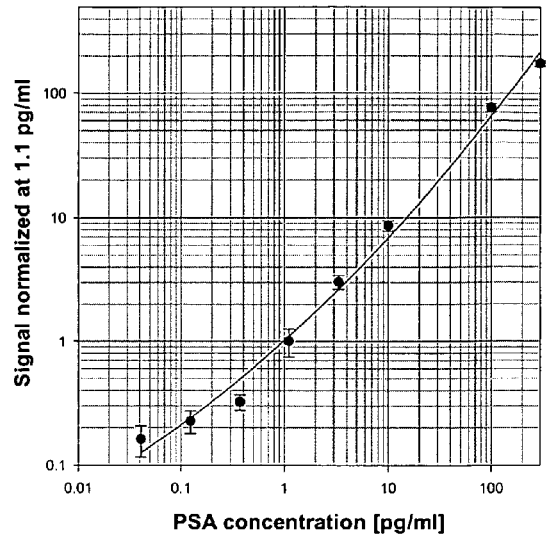
Fig. 36 : Super-ELISA for PSA.
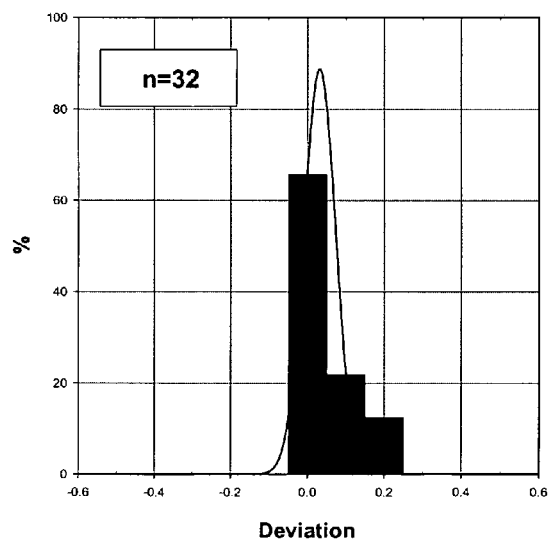
Fig. 37 : Reproducibility of Super-ELISA for PSA at 0.37 pg/ml.
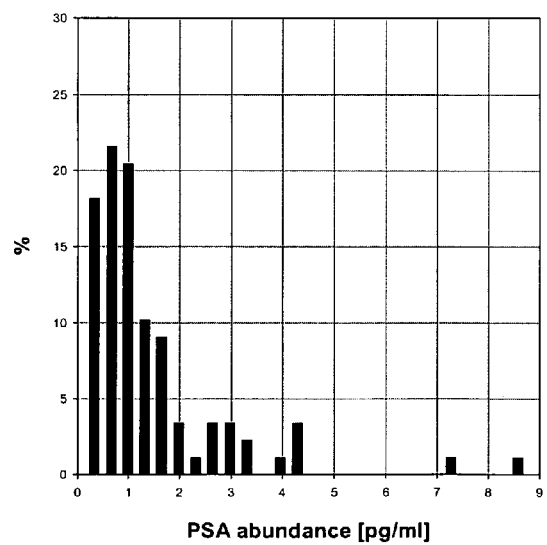
Fig. 38 : Distribution of PSA abundance in serum samples from 88 healthy women (age 20-100 years).

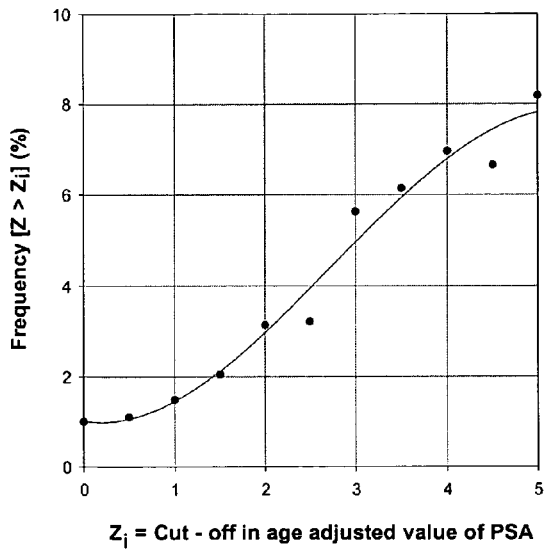
Fig. 39 : The ratio of probabilities for PSA level with $Z > Z_{cut-off}$ ; for healthy and non-treated breast cancer women.
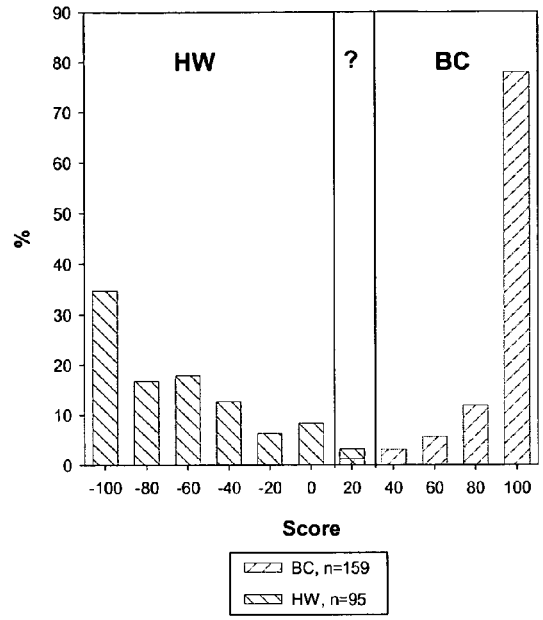
Fig. 40 : Score using optimal weights (OW)
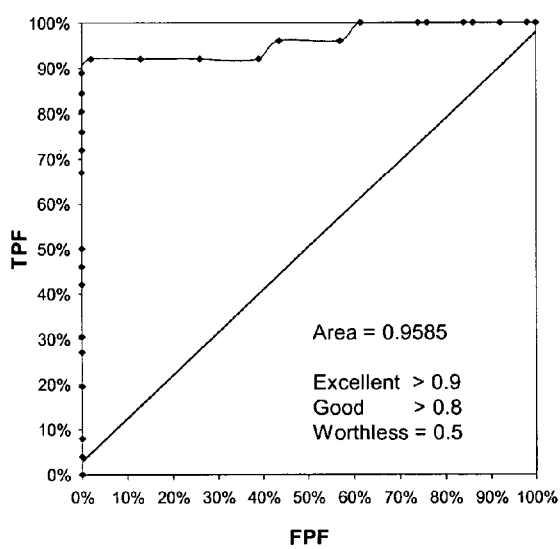
Fig. 41: ROC Curve for breast cancer
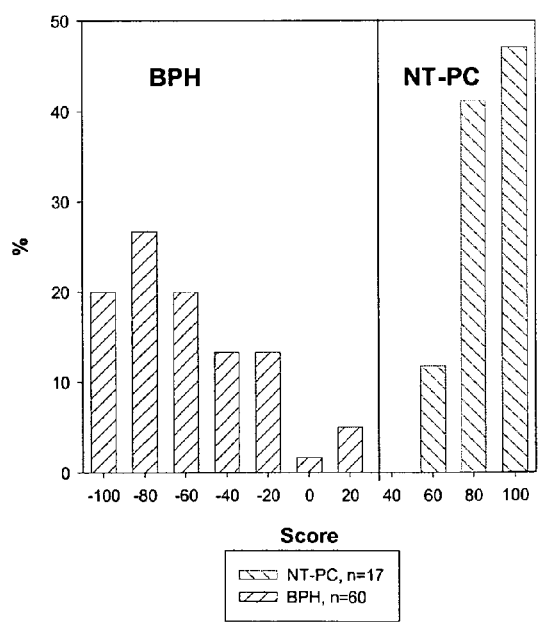
Fig. 42 : Identification of BPH vs. prostate cancer using six biomarkers

SUPERSENSITIVE IMMUNOASSAYS

BACKGROUND OF THE INVENTION

The immunodiagnostics: Traditional biomedical diagnostics have been structured around the analysis of a singular biomarker. The recent knowledge of the complexity and redundancy of protein networks and their changes during cancer progression suggest that the required sensitivity and reliability of such a diagnostics is possible only if a large number of biomarkers are quantitated concurrently. Such "panels" of biomarkers are needed to increase the specificity of the diagnostics. Even more importantly, most of these new biomarkers will be at much lower abundances than currently used markers, and many of them may be down regulated rather than up-regulated proteins. The limited sensitivity of prior-art immunoassays such as ELISA makes the use of additional cancer biomarkers difficult. More sensitive methods of biomarkers detection are required.

The diagnostic proteomics: It is too early to judge how many biomarkers should be used for any particular class of diseases. For example, in prostate or breast cancer, there are about 20 proteins whose abundance correlates with cancer. As such, the diagnostic panel(s) could be expected to feature about half of these putative biomarkers. However, one will need also to establish the immunologic status of a patient, e.g. quantitate 10-20 cytokines. Thus, one may need to quantitate up to 50 proteins concurrently. These type of studies are usually described as "diagnostic proteomics" and use the antibodies microarrays (P-chips).

As stated above, a majority of new biomarkers will be low abundance proteins. Thus, immunoassays with the highest sensitivity need to be used. The use of such super-sensitive immunoassays for the detection of markers will demand a considerable amount of biological material to be analyzed in an assay. A typical single immunoassay is performed in duplicate on a 200 microliter sample. With 32 samples, this leads to the need to obtain more than 10 ml of biological material, which in the biomedical applications is often difficult. Thus, the size of sample dedicated to a given target should be smaller (about 25 microliters). However, this leads to a need of an eight-fold higher assay sensitivity. For more than about 10 targets, the use of P-chips/MPD is critical and the need for high sensitivity is at a premium.

The need for improved sensitivity of immunoassays: Typically, the immunodiagnostic procedures are performed on relatively easily accessible physiologic fluids as blood, urine, saliva or breath condensate. In these situations it is possible to obtain a few milliliters of biological sample. However, there are also another situations, when only "forensic" sample of less than 10 microliter is available, e.g. in the case of needle biopsy.

The most important aspect of immunodiagnostics is the differentiation between the limit of detection (LOD) and limit of quantitation (LOQ). For assays such as ELISA, the limit of detection is typically a factor of few better than the limit of quantitation. Thus, for typical ELISA with LOD=1 pg/ml, reliable quantitation can be achieved in the range of 3-5 pg/ml. However, when the detection of proteins at 0.1 pg/ml is attempted, the ratio (LOD/LOQ) may considerably increase, i.e. at very low abundances quantitation becomes increasingly difficult. This can be traced to both the basic sources of non-specific biological backgrounds and the basic properties of rare processes when Poisson rather then Gaussian distributions are of importance.

The classical immunoassays such as ELISA achieved the 1 pg/ml sensitivity. A typical protein with the molecular weight (Mw) approximately equal to 20 kDaltons is equivalent to approximately $3 \times 10^7$ molecules or $5 \times 10^{-17}$ Mole. For many years this sensitivity has been considered to be sufficient for almost all biomedical tasks. In recent years, however, many new challenges in biomedical diagnostics suggest that a few hundred-fold increase of sensitivity is required for optimal sensitive detection. The biomedical situations which justify such dramatic increases in the sensitivity of immunodiagnostics can be divided into several categories:

Detection of viral and bacterial pathogens with a few copies per milliliter of blood;

Detection of very low abundance of physiologically potent proteins, e.g. cytokines;

Detection of proteins across the physiologic barrier, e.g. in blood not in CSF and in breath condensate rather than in blood; and Detection of rare, e.g. post-translationally modified form of the protein.

In all these situations the detection sensitivity of a few hundred times better than prior-art immunoassays (such as ELISA) is necessary. They are illustrated in the "Applications" section below by examples of biomedical diagnostics tasks that require improved sensitivity. The main interests are in:

Obtaining reliable information about low abundance factors influencing the immune system, e.g. for autoimmune diseases;

Applications in oncology;

Ultrasensitive and low cost diagnostic of infectiouse diseases; and

Applications in neurodegenerative diseases.

Two main trends in diagnostic proteomics: There are currently two main trends in diagnostic proteomics: extreme multiplexing vs. extreme sensitivity. With extreme multiplexing, a very large number of biomarkers are used but detection sensitivity is low. In currently existing antibody-based P-chips, information on about 100 biomarkers can be obtained with achievable limits of detection of about 5-10 pg/ml. In the "flow-cytometry derived" Luminex Inc. system, the sensitivity is between 10-50 pg/ml depending on the target. The reagents exist for about 100 targets, and a sub-set of about 50 is typically used for biological studies. In SELDI, the fragments of proteins can be detected at 100-200 pg/ml and then information about proteins can be indirectly obtained. SELDI has an advantage that not much information is required at the study initiation. However, as shown by the last 2-3 years of the diagnostic proteomics activities, the disadvantages of such diagnostic are lack of reliability, lack of comparison between groups, uncertain calibration, limited specificity and high cost.

According to the second school of thought, the detection of high abundance, mainly housekeeping proteins is a vestige of the past. The focus is now on an application tailored sub-set of low abundance biomarkers, typically the signaling proteins. In this case extremely high sensitivity is required. Previously it has been expected that this sensitivity's cut-off is at 0.5 pg/ml. my study showed the considerable advantage of supersensitive, i.e. down to 10 fg/ml, techniques. The ultimate sensitivity and optimal selection of biomarkers is used to compensate for the relatively low number of biomarkers.

The example: biomarkers for oncology: My studies show that detection of very low abundance proteins works well in detection of breast cancer, prostate cancer and melanoma. I evaluated this method using data from IA/MPD, Super-ELISA and a Luminex device. For optimal system, one needs to elucidate sensitivity and how many markers are needed. I evaluated the predictive power of different proteins as melanoma biomarkers based on the pioneering data of Dr. A. Lokshin, who used the Luminex-based measurement of over 70 biomarkers involving three cohorts: healthy individuals (n=44), pre-therapy melanoma patients (n=179) and post-therapy melanoma patients (n=172). For a number of important biomarkers, e.g. IL-1$_{beta}$, IL-6, IL-2, TNF$_{alpha}$, the Luminex devia is far from optimal. It can detect these biomarkers in less than 20% of healthy patients and less than 50% of melanoma patients. Also, a large number of outliers are observed.

FIG. 1 presents the averages over two cohorts for the above referenced 70 biomarkers. Note, that 90% of points are very close to the 45 degree line, i.e. have a very low predictive power when only averages are compared. Only seven biomarkers, all low abundance proteins, have a high predictive power. These are IL-6, IL-8, TNF$_{alpha}$, VEGF, MP1$_{alpha}$, MP1$_{beta}$ and MPA. I analyzed the distributions for these variables and demonstrated that IL-8 is the best single biomarker, with about 60% predictive power. Using prior-art methods of biostatistics and all 70 biomarkers, the detection sensitivity is at about 75%. Using my novel correlation-based method I achieved 90% sensitivity and specificity using only seven biomarkers. I expect, that when a more sensitive method is employed that has a better detection limit than Luminex, e.g. IA/MPD or Super-ELISA, the sensitivity and specificity can be further improved. The important point is that proteins with abundance above 50 pg/ml do not contribute significantly to the assays predictive power. On the other hand, a few carefully selected low abundance proteins provide reliable assay.

The tissue vs. systemic response biomarkers: Molecular diagnostics, especially as applied to oncology, is largely dependent on pathological information. Thus, the majority of biomarkers were discovered by differentially staining the tumors vs. healthy tissue. Only recently, the methods of discovery proteomics have been used to elucidate the differentially displayed proteins. Thus, the majority of available tumor markers are either a cytosolic or membrane proteins. Only a very small fraction of them are secreted proteins. These "tissue" biomarkers can be quite specific pathologically and yet almost useless when blood or other physiological fluids are used. There are strong barriers between the tissue and intersitial material and then between the tissue and blood. Thus, the abundance of tissue biomarkers in blood, e.g. serum, may vary greatly from patient to patient. Such tissue markers are organ and disease specific but are very difficult to quantitate because transfer through the barriers is a very complicated process.

Another class of biomarkers are the proteins which are involved in systemic response to disease. These can be modulators of immune response (cytokines), angiogenesis factors (AFs) or chemokines. There is a large sub-set of tumor infiltrating lymphocytes (TILs) that are chemo-attracted to tumors. These TILs, produce the cytokines or AFs inside the tumor. Locally, their concentration may be considerable, even if it is at a much lower level at blood. The person-to-person variation, however, is expected to be much lower than for tissue biomarkers. In a sense, cytokines/AFs/chemokines are "preferred" messengers and evolution permitted the development of many channels by which they efficiently propagate across the organism. For example, circulation of cytokines is not significantly attenuated by the brain-blood barrier. Obviously, these systemic response biomarkers are less specific than tissue biomarkers. The immune system evolved to respond by initiation of pro-inflammatory cascade of cytokines (IL-1$_{beta}$, IL-6, TNF$_{alpha}$) in case of microbial attack. The same mechanism is used to recognize/eliminate metastatic cells in cancer and is a crucial element of autoimmune cascade in asthma or arthritis. Thus, the measurement of a single cytokine is not very informative but an immunoprofiling can be specific.

The important aspects of using systemic response biomarkers is that they can be both down- and up-regulated. Furthermore, they can be strongly dependent on age and stage of disease. Finally, cytokines are the most potent signaling molecules. They are found in blood at sub-pg/ml levels and the ultimate sensitivity methods are necessary for their quantitation.

We implemented an innovative strategy of molecular diagnostics that synergistically used tissue and systemic response biomarkers. The systemic biomarkers can be divided into four sub-classes: pro-inflammatory cytokines, anti-inflammatory cytokines, angiogenesis factors and others. For each case, the quantitation of a plurality of factors is necessary for robust molecular diagnostics. Most important, all cytokines should be measured in all individuals. To achieve this, a group of novel, super-sensitive immunoassays (IA/MPD, Super-ELISA, RGIA) have been developed. The proposed method works only when a sensitivity better than 0.1 pg/ml is achieved. My group is the first worldwide to achieve this landmark sensitivity.

New methods of bioinformatics are necessary for analysis of biomarker patterns in oncology: Initially I expected that analysis of the data obtained using my super-sensitive methods of diagnostic proteomics would be possible using existing methods of biostatistics. Because my data shows that the distributions of almost all biomarkers are highly age-dependent and strongly non-Gaussian, I documented that the multi-dimensional correlations between biomarkers have a much higher predictive power than the distributions of any and each biomarker analyzed separately. We, therefore, developed a correlation based software to implement this new type of biostatistical analysis. This package contains the data input, calculations and sophisticated presentation software using wavelet and 3D modeling to facilitate the understanding of the correlations in obtained data sets. I believe that these programs may have many applications when any methods of immunodiagnostics and diagnostics proteomics are used, and that such a coordinated package of programs may be an important element of commercialization.

SUMMARY OF THE INVENTION

Traditional biomedical immunoassay diagnostics for cancer, autoimmune, infectious and/or neurodegenerative disease identification have been structured around the analysis of a singular biomarker. However, the trend in improving the reliability of these diagnostics is now turning to the analysis of a large number of biomarkers, which when quantitated concurrently as "panels" of biomarkers, can increase the specificity of the diagnostics. Additionally, most of the new biomarkers are at much lower abundances than currently used markers, and many of them may be down regulated rather than up-regulated proteins. As such, the sensitivity limitations of prior-art immunoassays techniques, such as ELISA with an LOD of 1 pg/ml, make the use of these additional disease related biomarkers very difficult. In fact, my study has demonstrated that biomarkers with highest predictive power are low abundance proteins. Consequently, immunoassays with the highest sensitivity need to be used, and new challenges in biomedical diagnostics suggest that optimally a few hundred-fold increase in sensitivity is required.

The superior sensitivity of MPD was essential during the development of my assays and allowed us to study and evaluate the different sources of background down to a few fg/ml level. Biological backgrounds can be divided into: (1) background due to cross-reactivity of antibodies (BAb); (2) background due to cross-reactivity of streptavidin (BStrep); and (3) background due to cross-reactivity with molecules of biological matrix, e.g. blood (NSBB). The reduction of these biological backgrounds was key in the development of IA/MPD, RGIA and my Super-ELISA protocols. I disclose herein below the methods of background rejection which enabled me to reach LODs of better than 50 fg/ml.

Currently, the majority of available tumor markers are either cytosolic or membrane proteins. Only a small fraction of them are secreted proteins. Therefore, the abundance of tissue biomarkers in blood, e.g. serum, may vary greatly from patient to patient. Such tissue markers are organ and disease specific but are very difficult to quantitate because transfer through the blood/tissue-organ barriers is a very complicated processes. Another class of biomarkers are the proteins which involve the systemic response to disease. These can be modulators of immune response (cytokines), angiogenesis factors (AFs) or chemokines. Cytokines are "preferred" messengers and evolution permitted the development of many channels by which they efficiently propagate across the organism. For example, circulation of cytokines is not significantly attenuated by the brain-blood barrier. The important aspect of using systemic response biomarkers is that they can be both down-regulated and up-regulated. They can also be strongly dependent on age and stage of disease. Cytokines are the most potent signaling molecules and, being found in the blood/serum at sub-pg/ml levels, necessitate the use of ultra-sensitive methods for their quantitation.

An innovative strategy of molecular diagnostics has been found that synergistically uses tissue and systemic response biomarkers. The systemic biomarkers can be divided into four sub-classes: pro-inflammatory cytokines, anti-inflammatory cytokines, angiogenesis factors and others. For each case, the quantitation of a plurality of factors is necessary for robust molecular diagnostics. Most importantly, the key is to be able to measure multiple cytokine in all individuals. To achieve this, a group of proprietary, super-sensitive immunoassays (IA/MPD, Super-ELISA, RGIA) have been developed. The proposed method works only when a sensitivity better than 0.1 pg/ml is achieved. This invention discloses how to develop the immunoassays which detects multiple cytokines in all patients.

Data I have generated shows that the distributions of many biomarkers are highly age-dependent and strongly non-Gaussian. Consequently, existing packages of biostatistical software, which deal predominantly with Gaussian distributions, are not applicable. I documented that multi-dimensional correlations between biomarkers have a much higher predictive power than the distributions of any individual biomarker analyzed. Therefore, I also disclose an innovative, correlation-based algorithm that is comprised of a suite of programs to implement the new type of correlation-based software. This package contains the data input, calculations and sophisticated presentation software using wavelet and 3D modeling to facilitate the understanding of the correlations in the obtained data sets. Optimal methods of using this new class of algorithms are disclosed as being specifically optimized for oncology applications with excellent sensitivity/specificity achieved in the detection of breast cancer, prostate cancer, ovarian cancer and melanoma.

We disclose the use the supersensitive assays (Super-ELISA, IA/MPD) and sophisticated methods of statistical analysis as described above specifically in detection of breast cancer. I measured 159 samples of serum from two cohorts of women with untreated breast cancer, and ninety-five (95) samples from putatively healthy women. I measured PSA, $TNF_{alpha}$, IL-6, IL-8 and VEGF for all samples. For some samples I also measured $IL-1_{beta}$ and IL-4. The sensitivity and specificity of the detection of breast cancer (BC) in the studied cohorts using five specific biomarkers, i.e. PSA, $TNF_{alpha}$, IL-6, IL-8 and VEGF, achieved better than 95% sensitivity and specificity.

BRIEF DESCRIPTION OF THE DRAWINGS AND FIGURES

The features of the present invention will become more apparent when considered together with the following drawings wherein:

FIG. 1 is a graph showing averages for two cohorts of low abundance biomarkers

FIG. 2 is a drawing showing "sandwich" immunoassays for IA/MPD, ELISA and Super-ELISA FIG. 3 is a graph showing the sensitivity of IA/MPD, Super-ELISA and ELISA FIG. 4 is a graph showing the comparison of sensitivity of IA/MPD and ELISA targeting IL-1β

FIG. 5 is a graph showing reproducibility of IA/MPD for IL-1β.

FIG. 6 is a graph showing the comparison of sensitivity of IA/MPD and ELISA targeting IL-6.

FIG. 7 is a graph showing Super-ELISA for TNF using new colorimeter.

FIG. 8 is a graph art showing the reproducibility of Super-ELISA for Human TNF.

FIG. 9 is a graph showing Super-ELISA for IFN.

FIG. 10 is a graph showing reproducibility of ELISA for IFN.

FIG. 11 is a graph showing the distribution of IL-6 in healthy women.

FIG. 12 is a graph showing the distribution of TNF in healthy women.

FIG. 13 is a graph showing the Super-ELSIA for L-8.

FIG. 14 is a graph showing the reproducibility of Super-ELISA for IL-8.

FIG. 15 is a graph showing the average level of IL-8 in BC and HW cohorts.

FIG. 16 is a graph showing the distribution level of IL-8 in BC cohort.

FIG. 17 is a graph showing the Super-ELISA for FGF1.

FIG. 18 is a graph showing the reproducibility of Super-ELISA for FGF1 at 0.1 pg/ml.

FIG. 19 is a graph showing the Super-ELISA for VEGF concentrations.

FIG. 20 is a graph showing the reproducibility of Super-ELISA for VEGF at 0.1 pg/ml.

FIG. 21 is a graph showing the distribution of breast cancer women.

FIG. 22 is a graph showing the average level of VEGF in BC and HW healthy cohorts and age dependence.

FIG. 23 is a diagram showing biological matrix independent backgrounds.

FIG. 24 is a diagram showing biological matrix dependent backgrounds.

FIG. 25 is a graph showing antibody qualities for six IA/MPDs.

FIG. 26 is a graph showing IA/MPD results with different washing.

FIG. 27 is a graph showing Super-ELISA for PSA using two washing conditions.

FIG. 28 is a graph showing the use of ultrasound wash to improve sensitivity in wells, microtiter format.

FIG. 29 is a graph showing IA/MPD using Mod 8 and Mod 4 assey buffers.

FIG. 30 is a graph showing the background as a function of $^{125}$I-streptavidin incubation time.

FIG. 31 is a graph showing shorter incubation time with $^{125}$I-streptavidin.

FIG. 32 is a graph showing that the slow roll processing improves sensitivity.

FIG. 33 is a diagram showing amplified IA/MPD.

FIG. 34 is a diagram showing amplified Super-ELISA.

FIG. 35 is a graph showing TNF alpha concentrations.

FIG. 36 is a graph showing PSA concentration.

FIG. 37 is a graph showing the reproducibility of Super-ELISA for PSA.

FIG. 38 is a graph showing the distribution of PSA abundance in serum samples from healthy women.

FIG. 39 is a graph showing the ratio of probabilities for PSA levels with $Z > Z_{cut-off}$ for healthy women and non-treated breast cancer women.

FIG. 40 is a graph showing breast cancer scoring.

FIG. 41 is a graph showing an ROC Curve for breast cancer.

FIG. 42 is a graph showing identification of BPH vs. prostate cancer.

DETAILED DESCRIPTION OF THE INVENTION

Towards Ultrasensitive Immunoassays

The classical "sandwich" immunoassays are described in FIG. 2. The appropriate surface, usually plastic, is coated by capture antibodies. Typically, a very large excess of antibodies, approximately $10^5$ to $10^6$, is used. After the appropriate blocking, the biological sample is incubated and specific interaction between the selected epitope on the protein and antibody (Ab) immobilizes the targeted protein on plastic. The Ab-epitope interaction is strong enough to survive the stringent washing. Subsequently, the labeling antibody specific to other epitope on the targeted protein is added. Current methods use very large excess of labeling antibodies, typically factor of $10^4$ to $10^5$. These antibodies can be labeled or they can carry a moiety that can be targeted by yet another immunoreagent that is labeled. For example, the labeling antibody can be labeled with a radiolabel or can be conjugated to horse radish peroxidase (HRP). Often the antibody itself carries a linker moiety that can be subsequently attached to an appropriate labeled moiety. For example, the labeling Ab can be biotinylated and then one can use $^{125}$I-streptavidin or streptavidin-HRP.

Current immunodiagnostics are limited by the analytic sensitivity of read-out instruments and non-specific biological backgrounds. There is a long tradition of improving the signal in sandwich immunoassays. For example, the labeling antibody can be multi-labeled with radioactive $^{125}$I or other radiolabel. On other hand, when the enzymatic labels such as HRP are used, generation of assay developers concentrated on improving the enzyme turnover. The reaction conditions and substrates used have been considerably improved. The substrates are now so optimized that progress in signal amplitude is very slow.

Many groups tried to increase the signal in sandwich immunoassays by putting a large number of labeling moieties on an appropriate linker molecule. One such method used streptavidin based reagents (strep-reagents) with biotinylated Abs. The standard use is strep-polyHRP with different forms being used, i.e. strep-HRP(20), strep-HRP(40) and strep-HRP(80), all of which are widely commercially available. It has been recently realized, however, that use of such signal amplifiers leads to new sources of artifacts.

As the signal amplifications leads to new sources of background interferences, the optional method is to increase the analytic sensitivity of the read-out instruments. For example, I previously developed the ultrasensitive multi-photon detection (MPD) instrumentation (see U.S. Pat. Nos. 6,225,132, 5,866,907, and 5,854,084) (see description below). This sensitive instrumentation permitted BioTraces to better understand and identify sources of background and implement new sensitive methods of biological background rejection. My ability to eliminate most of the background was important to BioTraces' ability to detect the presence of biomarkers with better sensitivity because immunoassay signal amplification is useful only if signal/background is improved. I documented that it is better to diminish background rather than increase the signal. This focus on the rejection of different sources of background enabled development of two super-sensitive immunoassays: MPD enhanced immunoassay (IA/MPD) and Super-ELISA assay. The historical progress is documented in FIG. 3. Note that I achieved the landmark sensitivities of 1 fg/ml and 10 fg/ml for IA/MPD and Super-ELISA, respectively. More recently, I developed Reverse Geometry Immunoassay (RGIA).

The understanding of sources of biological background has been crucial in this new implementation of immunoassays. The understanding of "hidden" sources of background has been made possible by the MPD instrumentation. Thus in following, I describe the MPD instrumentation and the performance of MPD enabled immunoassays. The MPD instrumentation is already covered by series of existing and pending patents. This disclosure focus on the novel methods of biological background recognition and rejection that was enabled by MPD also enabling the development of Super-ELISA in which the optical detection is used.

Multi Photon Detection (MPD): As stated above, MPD is a patented detection system for the measurement of ultra-low amounts of selected radioisotopes. MPD enhanced biomedical methods have several advantages over existing methods: 1,000-fold improvement in sensitivity, enabling measurement of previously undetectable amounts of target substances; high dynamic range (7-8 decades), eliminating the need for sample concentration or dilution; cost savings due to decreased amounts of reagents and reduced time for testing. With sensitivity better than a thousand atoms of $^{125}$I, MPD marks a new milestone in detection where quantitation of sub-zeptomole amounts of biomaterial is possible. MPD require sub-pCi of isotope, i.e. about a 100-times less activity than in a glass of water. MPD can quantify amounts of compounds as low as a hundred molecules, i.e. at sub-zeptomole ($<10^{-21}$ mole per sample) levels. Appropriate biological procedures coupled with MPD readout (IA/MPD) provide an extremely sensitive analytical technique that is applicable to the detection and quantitation of many analytes. Immunoassays with MPD readout (IA/MPD) are new, ultra sensitive techniques for the detection and quantitation of proteins. The limits of detection (LOD) are about 500-fold better than the prior-art techniques. For proteins, IA/MPD sensitivity is approximately 40 zeptomole per milliliter ($40 \times 10^{-21}$ mole/ml).

MPD distinguishes the highly specific decay signature of certain radioisotopes from the various forms of naturally occurring background radiation; MPD reduces the measurement background to less than one event per day. Over a hundred isotopes are compatible with MPD. Of these, $^{125}$I is the most commonly used. MPD can identify and distinguish among several different isotopes in the same sample. This is possible because each isotope emits decay photons with different characteristic energies. This multicolor capability permits simultaneous measurement of several different analytes within the same sample.

MPD—Instrumentation: srMPD/MT96 and srMPD/MT384 instruments allow rapid automated measurement of microtiter plates with 96 or 384 wells. So the development of commercial IA/MPD kits to provide non-hazardous, ultra sensitive immunoassays has obvious commercial appeal. The advantages of this methodology are that the IA/MPD is rapidly performed; the assay is similar to ones employed in most biomedical analysis laboratories and the instrumentation, while electronically sophisticated, is easy to use.

We developed and tested my high spatial resolution MPD Microarray Reader (MPD-MR). I prepared the pattern of 13×13 spots regularly placed on 1.8 cm×1.8 cm surface. Each spot was about 1 attomole of radiolabeled streptavidin. The excellent spatial resolution and reproducibility was documented. In fact, the read-out reproducibility is much better than the spot-to-spot reproducibility of standard micropipetting. At larger surface I created an array of 32×32 spots, each of less than 1 attomole. To study the dynamic range at sub-attomole level, I placed spots by micropipetting. I documented my ability to quantitate the spots down to 0.1 attomole with no cross-talk between the neighboring spots even for this very low activity.

We developed MPD Imager/400 and MPD Imager/1.6K, which measure gels with size up to 24 cm×24 cm. MPD Imager/400 has a position sensitive detector that reads the sample at 400 pixels concurrently, and the secondary detector, which produces coincident trigger for coincident events. MPD Imager 1.6K has four position sensitive detectors and four secondary detectors. MPD Imagers detect spots with activity about 10 zeptomoles of $^{125}$I. They can distinguish one radioactive isotope from another and can build the images in different isotopes. The special package of off-line processing software is capable of finding spots using both images: coincident and non-coincident.

MPD enhanced immunoassays: A new, super sensitive immunoassay (IA/MPD) provides quantitative measurement of biological substances at levels as low as a femtogram/ml, i.e. sub-attomole sensitivities of IA/MPDs for several cytokines.

Like an ELISA, an IA/MPD is an antibody sandwich capture assay in which one antibody is immobilized and serves to capture a ligand while a second antibody binds to a different epitope on the ligand and is used for quantitation. In ELISA, the second antibody is labeled with biotin so that a streptavidin/enzyme conjugate can be used to produce the signal. In D, however, quantitation of bound ligand/detector antibody is accomplished by using $^{125}$I-streptavidin. The amount of bound tracer antibody is directly proportional to the amount of bound ligand. The extraordinary sensitivity of the MPD instrument allows a reduction in the assay volume and amount of reagents needed, including the tracer antibody. Specialized blocking and assay buffer reagents have been developed to reduce nonspecific biological background (NSBB), which produces about a 1,000-fold greater sensitivity than is possible with ELISA.

Our studies compared the IA/MPD to prior art immunoassay methods. The unprecedented sensitivity of a family of IA/MPDs for cytokines (IL-1$_{beta}$, IL-4, IL-6, IL-10, IL-11, IL-12, IL-18, TNF$_{alpha}$) has been documented. These quantitatively accurate MPD immunoassays have a sensitivity of about 1 fg/ml, i.e. better than 0.1 attomole/ml, which is below the natural radioactive background. Essential to the success of each IA/MPD has been my work on developing protocols and proprietary reagents for the reduction of nonspecific biological binding. In Table 1, the landmark 1 fg/ml sensitivity of ELISA, Super-ELISA, Reverse Geometry Immunoassay (RGIA) and IA/MPD for a plurality of proteins is documented. The IA/MPD is most sensitive.

TABLE 1

| | ELISA, Super ELISA, RGIA and IA/MPD Sensitivities (for Selected Proteins LOD in pg/ml) | | | | | | |
|---|---|---|---|---|---|---|---|
| Target | PSA | p24 | IL-1$_{beta}$ | IL-4 | IL-6 | IL-10 | TNF$_{alpha}$ |
| ELISA | 5.0 | 1-2 | 0.5-3 | 0.2-3 | 0.2-1 | 0.5-3 | 3-10 |
| Super-ELISA | 0.1 | 0.075 | 0.05 | 0.05 | 0.02 | 0.05 | 0.02 |
| RGIA | 0.05 | — | 0.01 | — | 0.01 | — | 0.01 |
| IA/MPD | 0.01 | 0.001 | 0.001 | 0.001 | 0.002 | 0.01 | 0.005 |
| Improvement* | 1,000 | 1,000 | 200 | 200 | 500 | 150 | 1,000 |

*Compares IA/MPD and ELISA

As mentioned above, the MPD enhanced immunoassay (IA/MPD) is a super sensitive technique that achieved the landmark 1 fg/ml sensitivity. However, there was a need to improve the sensitivity of other sandwich assays. I developed two such assays: Super-ELISA and Reverse Geometry Immunoassay (RGIA).

Super-ELISA: The sensitivity of current "sandwich techniques" is limited by a plurality of sources of biological background. My effort in development of IA/MPD permitted the better understanding and removal of the sources of biological background. I developed a specialized ELISA assay that uses streptavidin-polyHRP as label but implements all methods of background rejection procedures developed for IA/MPD. I call such a technique Super-ELISA. I stress that even though the final procedure does not use the MPD instruments, the Super-ELISA is MPD enabled. In many steps of assay optimization, I use the MPD instrumentation to optimize the format and reject a particular source of background.

The IA/MPD and Super-ELISA are similar techniques; the important differences are in labeling and read-out steps. For IA/MPD I use $^{125}$I-streptavidin and MPD instruments. For Super-ELISA I use the streptavidin-polyHRP(n), where n=20, 40 or 80 and I use a colorimetric plate reader. Thus, most sources of biological background are the same, with the possible exception of background from $^{125}$I-streptavidin versus streptavidin-polyHRP sticking to the plastic substrate. Background due to stickiness of streptavidin dominates the overall biological background. I developed a series of Super-ELISA assays for a selected targets for which IA/MPD were already available achieving LOD=50 fg/ml and reasonable reproducibility. More recently, my sensitivity has improved towards 10 fg/ml.

In IA/MPD, I used an instrument that is about 1,000-fold more sensitive than typical colorimetric plate readers. This permitted us to better understand the sources of biological background and remove them by changes in biological procedures. In my IA/MPD assays, the level of non-specific biological background is at about 1 fg/ml. Proprietary methods of biological background reduction permit us to initiate the search for further improvements of Super-ELISA. The comparison of my IA/MPD data shows that the factor 10-20 difference in LOD in favor of IA/MPD is because the existing "microtiter plate" calorimeters are not sensitive enough. I believe that ultra-low biological backgrounds achieved in IA/MPD development allow a further few-fold improvement of sensitivity of Super-ELISA. Practically, there are two main methods—amplify the signal or improve the analytical sensitivity of devices sensing the change of color. Both methods have been successful and for a model protein, $TNF_{alpha}$ I demonstrated Super-ELISA with about 10 fg/ml sensitivity. Thus, I demonstrated that Super-ELISA is at least 50 times more sensitive than "classical" ELISA.

Reverse Geometry Immunoassay (RGIA): RGIA is a sandwich assay with colorimetric readout and uses an ordered array of "pins". It should be stressed that RGIA uses pins that are much smaller than the surface of the wells in a 96-wells microtiter plate. In fact, the area at which Abs can bind is considerably smaller than the surface of wells of even the 384-wells microtiter plate. Subsequently, the amount of the capture Abs that can be loaded on such pins is very low. This leads to a signal substantially lower than the signal in ELISA or Super-ELISA. In RGIA, streptavidin-HRP is replaced with streptavidin-polyHRP to bring the signal above the analytical sensitivity level of colorimeters. However, use of a much larger labeling molecule (2 MegaDalton vs. 60 kiloDalton) leads to a considerable increase in NSBB.

The use of 96-wells microtiter plates is very convenient but does lead to a diminished efficiency of wash. The geometry of RGIA is more versatile than microtiter plates and is compatible with concurrent measurements of up to 12 different markers from the same blood sample. Briefly, these derivatized plastic pins are aligned with the wells of the 96 wells microtiter plate. The challenge was the available surface at the top of each pin being about 5 $mm^2$ as compared to about 30 $mm^2$ for the 96 wells microtiter. With this "pin" geometry, a more stringent wash is possible which subsequently leads to a considerably smaller non-specific biological background. In this geometry, the use of ultrasound washing is very efficient. Additionally, a customized plate has been developed that incorporates the use of the both the "x" and "y" axis slots for colorimetric readout purposes thus reducing the number of required liquid transfers needed for analysis. I also developed a RGIA compatible with 384 samples format. RGIA uses streptavidin-HRP(80), rather than streptavidin-HRP(20) used in the Super-ELISA due to diminished signal. An additional step of blocking is also employed using a proprietary super-blocker before applying streptavidin-polyHRP. Optionally, streptavidin-HRP(20) could be used in the amplification step followed by incubation of biotinated Abs targeting HRP. RGIA was developed for six biomarkers (i.e. PSA, $TNF_{alpha}$, $IL-1_{beta}$, IL-6, IL-8 and VEGF). We've demonstrated that RGIA has a sensitivity of 10-20 fg/ml, i.e. is a factor of 2-3 times more sensitive than Super-ELISA and about 100-fold more sensitive than typical prior-art ELISA.

Immunoassays for Cytokines and Angiogenesis Factors

Cytokines: In this section I provide some examples of use of the new supersensitive methods for quantitation of cytokines.

IA/MPD for IL-1 beta: Using NUNC microsorb microtiter plate format and CLB antibodies, the standard curve of this IA/MPD ranged from 1 fg/ml to 100 pg/ml. The background is strongly dependent on the assay conditions, especially the washing conditions. Optimization of pH and the use of appropriate blocking procedures are also mandatory. ELISA and IA/MPD for IL-1 beta were compared (see FIG. 4). The limit of detection (LOD) in IA/MPD is 1 fg/ml, i.e. 500-fold better than commercially available ELISA assays. IA/MPD for $IL-1_{beta}$ is very reproducible, with a CV of about 20% down to a few fg/ml. In the FIG. 5 the distributions of measurements at the level of 10, 100 and 1,000 fg/ml of $IL-1_{beta}$ were plotted, and all distribution curves are close to a Gaussian.

IA/MPD and Super-ELISA for IL-6: Using NUNC 96-well microtiter plate format and CLB antibodies, the standard curve of this IA/MPD ranged from 2 fg/ml to 100 pg/ml. ELISA and IA/MPD for IL-6 are compared in FIG. 6; the limit of detection (LOD) in IA/MPD is 1 fg/ml, i.e. 500-fold better than commercially available ELISA assays. IA/MPD for IL-6 is very reproducible, with a CV of about 20% down to a few fg/ml. The Super-ELISA for IL-6 has been first developed using the streptavidin-HRP(20). However, using this reagent I achieved only 50 fg/ml limit. I also tried the amplified Super-ELISA concept and improvement to 30-40 fg/ml has been achieved.

IA/MPD and Super-ELISA for TNFalpha12: I developed the IA/MPD targeting $TNF_{alpha}$ with a few fg/ml sensitivity. I also developed Super-ELISA which achieved a landmark 10 fg/ml sensitivity. I studied a classical ELISA (using streptavidin-HRP(1)), my optimized Super-ELISA (using streptavidin-HRP(40)) and new amplified Super-ELISA (using two stages of amplification with streptavidin-HRP(20)). In all cases, the same substrate and plate reader has been used. Each step of amplification leads to about a factor five gain in sensitivity as demonstrated by the achieved limits of detection (LOD) of 100 fg/ml, 20 fg/ml and 10 fg/ml, respectively. More importantly, amplified Super-ELISA has excellent reproducibility (CV=20%) down to 10 fg/ml. I developed an improved colorimeter with about ten-fold better sensitivity than commercially available plate readers. This permitted 10 fg/ml sensitivity (see FIG. 7). To achieve this sensitivity, both the amount and time of application of streptavidin-polyHRP has been optimized. I also achieved an impressive reproducibility at 10 fg/ml (see FIG. 8).

$IFN_{gamma}$: I developed the IA/MPD and Super-ELISA targeting IFN-gamma with a sensitivity of 10 and 50 fg/ml, respectively (see FIG. 9). The reproducibility is about 15% at 100 fg/ml (see FIG. 10).

Applications of IA/MPD in Study of Cytokines:

$IL1_{beta}$: I studied distribution of $IL1_{beta}$ in serum of about 100 healthy controls. The sensitivity of assay had been about 0.05 pg/ml. The distribution curve is not compatible with Gaussian, however, it can be fitted by a 1/f type curve. It has a maximum below 50 fg/ml but extends to a few pg/ml. I note a surprisingly large dynamic range of at least 4 logs.

IL-6: I measured the distribution of IL-6 in serum of 160 women with breast cancer and 115 healthy women (HW) blood donors (see FIG. 11 for distribution of HW cohort). The lowest measured value is 0.02 pg/ml and the highest is 2 pg/ml. The distribution curve is compatible with Gaussian with the mean value of 0.1 pg/ml. I observed, however, a tail of outliers. Especially for breast cancer cohort there is often a large up-regulation of level of IL-6. However, when the outliers are removed, one observes a relatively low dynamic range of 20. All 30 samples have been reliably measured with Super-ELISA but only 20% can be measured with ELISA.

TNF$_{alpha}$: The distribution of TNF$_{alpha}$ in serum of 118 healthy women is shown in FIG. 12. The lowest measured value is 0.1 pg/ml and the highest is above 100 pg/ml. The low values part of distribution curve is compatible with Gaussian, with the mean value of 2 pg/ml. However, there is also a clear shoulder compatible with 1/f background and a tail of outliers. Please note that with exception of a few outlayers, there is a relatively low dynamic range of less than 50. Thus, TNF$_{alpha}$ may be a good proxy marker for any break-down of immune regulation process. All values out of about 280 donors (159 BC and 118 healthy women) has been reliably measured with Super-ELISA but only 40% can be measured with ELISA.

IFN$_{gamma}$: I measured the distribution of IFN$_{gamma}$ in serum of 100 healthy blood donors. The lowest measured value is 2.0 pg/ml and the highest is 30 pg/ml. The distribution curve is compatible with Gaussian, with the mean value of 10 pg/ml. A relatively low dynamic range of 15, suggest that IFN$_{gamma}$ may be a good proxy marker for studies of immune response. All values out of 50 were reliably measured with IA/MPD but only 60% were measured with ELISA.

Overall, I note that IA/MPD considerably improves the ability to study cytokine concentration differences between healthy and unhealthy individuals. Cytokines drive the immune response and generally can be classified as pro- and anti-inflammatory. These two classes are also connected with Th1 and Th2 type of immune response. My distribution studies using the supersensitive IA/MPD suggest yet another division between cytokines. The Type 1 cytokines, e.g. TNF$_{alpha}$, IFN$_{gamma}$ and IL-6 have a Gaussian distribution and relatively low dynamic range of abundance. The Type II cytokines, e.g. IL-1$_{beta}$ and IL-10 have strong non-Gaussian distribution and are characterized by very large concentration range. My effort will further study this interesting, new classification of cytokines. Such studies are enabled by the supersensitive IA/MPD and Super-ELISA.

Angiogenesis Factors (AFs): Tumors produce circulating factors that have the potential to be used as diagnostic markers for the presence of the tumor. These markers may be tumor type specific, angiogenic factors, or cytokines involved in the angiogenesis response to the tumor. Diagnostics based on just one marker yields too many false positives.

IL-8, FGF-1 & VEGF: I developed supersensitive immunoassays for the angiogenesis factors (AF), e.g. Interleukin-8 (IL-8), Fibroblast Growth Factor-1 (FGF-1) and Vascular Endothelial Growth Factor (VEGF). These AFs are expressed in many tumor types. Clinically relevant serum samples were screened for a plurality of biomarkers, including AFs, cytokines and PSA. The relevant serum samples included pre- and post-cancer treatment patients, and healthy control subjects. All together, I studied about 600 samples for three cancers: breast cancer, prostate cancer and melanoma. The work has been performed in collaboration with three leading cancer wards in the USA and one in England. Results were examined using a plurality of biostatistical tools and documented that my method has excellent sensitivity (>95%) and specificity (>90%). My study determined that a particular pattern of marker levels correlates with the presence of a particular tumor. These patterns are different for different tumors.

The best prior-art methods for detection of the diverse AFs have a limit of detection (LOD) of 10 pg/ml, 5 pg/ml and 20 pg/ml for IL-8, FGF1 and VEGF, respectively. Because of this relatively low sensitivity, with exception of VEGF, the AFs could be detected only in a small fraction of sera of healthy individuals. In fact, FGF1 could only be detected in less than 10% of healthy individiuals and IL-8 in about 30% of healthy individuals. I improved the sensitivity of immunoassays for IL-8, FGF1 and VEGF about a hundred-fold. The achieved limits of detection are provided in Table 2.

TABLE 2

Immunoassays for Angiogenesis Factors (AFs)

| Target | IL-8[pg/ml] | FGF1[pg/ml] | VEGF[pg/ml] |
|---|---|---|---|
| ELISA | 10 | 5 | 20 |
| IA/MPD | 0.05 | 0.05 | 0.1 |
| Super-ELISA | 0.1 | 0.1 | 0.3 |
| Improvement | 200 | 100 | 200 |

The linearity of my Super-ELISA assay for IL-8 is presented in FIG. 13. I note an excellent reproducibility down to 0.1 pg/ml (see FIG. 14). I also used IA/MPD for IL-8. With these assays I can detect IL-8 in sera of all of healthy individuals. I demonstrated that IL-8 is down regulated in breast cancer sera (see FIG. 15). I reliably measured IL-8 in sera of 150 breast cancer women (see distribution in FIG. 16.) Actually, I reliably detected IL-8 in about 400 sera from breast cancer, prostate cancer and healthy individuals.

The linearity of my Super-ELISA assay for FGF1 is presented in FIG. 17. I note an excellent reproducibility down to 0.1 pg/ml (see FIG. 18). I also used IA/MPD for FGF1. However, even with these assays I can only detect FGF1 in 80% of healthy individuals sera. I expect that an assay with 5 fg/ml sensitivity will be necessary to detect the level of FGF1 in sera of all, even down-regulated, individuals.

The linearity of my Super-ELISA assay for VEGF is presented in FIG. 19. I achieved an excellent reproducibility down to 0.1 pg/ml (see FIG. 20). The distributions in about 350 breast cancer, prostate cancer, BPH, prostatitis and healthy individuals have been reliably measured. The distribution in breast cancer women is presented in FIG. 21. I noted that in cancer patients the level of VEGF was upregulated and the age dependence should be taken into consideration (see FIG. 22).

MPD-enabled techniques can be used in P-chips/MPD to quantitate a large set of markers including PSA, CEA, CA-125, and other biomarkers. Additional factors, which are expressed by tumors but cannot be detected by prior-art, relatively low sensitivity diagnostics will also be studied. Testing on clinically relevant samples will be expanded. Once the importance of concurrent measurement of several of these biomarkers are confirmed, I will develop dedicated, supersensitive P-chips for quantifying a larger set of marker proteins with detection ranges from 0.01 to 500 pg/ml. Thus, low cost cancer diagnostics and therapy monitoring assay will become available.

Challenges of Ultrasensitive Immunodiagnostics

The challenge of biological background: The development of the supersensitive assays has been enabled by a plurality of innovative steps. Typically, two or three different methods of background rejection are used in the same immunoassay. Each leads to relatively small, a factor of few improvement of sensitivity. However, one can achieve the combination of optimization steps, when the sensitivity gains piles-up. The important steps are: optimization of the antibody capture systems; selection of optimal amounts of capture and labeling Abs; selection of optimal blocking and washing reagents, and improvement in signal-to-background ratio.

In IA/MPD but also in RGIA and Super-ELISA, nonspecific biological background (NSBB) is the factor limiting sensitivity. Decreasing NSBB represents an especially difficult challenge. The assay and wash buffers were tailored for IA/MPD. I use a serum-based assay buffer for binding of target protein to capture Abs immobilized on microtiter plate. A specialized assay buffer was used for binding of the detector antibody to the target proteins. Nonspecific sticking of the detector antibody is a source of the NSBB in IA/MPD's, which can be eliminated by adding proprietary reagents to the assay buffers. These buffers help stabilize the antibodies, promote binding and improve blocking. Importantly, I documented that the same proprietary reagents are "almost universal", i.e. they can be used to a large majority of target proteins I tested. Thus, the IA/MPD assays are performed in conditions compatible with the P-chip/MPD assay.

The enabling character of supersensitive MPD instrumentation permitted a breakthrough in understanding sources of biological background in sandwich immunoassays. The main limiting factor to assay sensitivity has been biological background and background due to non-specific sticking of streptavidin to plastic. Better blocking procedures as well as refined assay buffers helped to further decrease the biological background. Additionally, the biological background was reduced by using more stringent washing conditions. Most importantly, the background due to the non-specificity of streptavidin has been considerably decreased.

Sources of background and their elimination: The reduction of biological backgrounds (BBs) is a key to the development of IA/MPD and Super-ELISA protocols. The superior sensitivity of MPD was essential during the assay development to study the different sources of background down to the 0.1 fg/ml level. The biological backgrounds can be divided into: background due to cross-reactivity of antibodies (BAb); background due to cross-reactivity of streptavidin (BStrep) and background due to cross-reactivity with molecules of biological matrix, e.g. blood (NSBB). The attention of most assay developers has been on diverse sources of non-specific biological background (NSBB). I demonstrated that sensitivity for assays performed in buffer and serum, urine and milk are similar. The sources of background are illustrated in FIGS. 23 and 24.

Our progress in development of supersensitive immunoassays can be traced to systematic development of methods that remove the different groups of background. The numbers quoted in Table 3 are my best estimates based upon about 200 different experiments with eight different targets (TSH, p24, $TNF_{alpha}$, IL-1β, L-4, IL-6, IL-10 and PSA). About twenty different batches of $^{125}$I-streptavidin and streptavidin-poly-HRP have been tested. I used plastic microtiter plates from four different producers. I documented the advantages of NUNC microtiter plates and subsequently tested about six batches of these microtiter plates. I evaluated the NSBB in diverse physiological fluids, including human and cow milk, as well as human, rat and snake serum.

TABLE 3

Sources of backgrounds in IA/MPD assay (in fg/ml)

| Source of Background | 1998 | 2000 | 2002 | 2004 |
|---|---|---|---|---|
| BAb | 5-10 | 1 | 0.1 | 0.05 |
| BStrep | 5 | 2 | 0.5 | 0.2 |
| NSBB | 1 | 0.5 | 0.2-0.3 | 0.1 |
| Total# | 10 | 2 | 0.5 | 0.3 |

Total background equals the square root of sum of squares of each source of background Novel Methods of Rejecting Biological Backgrounds There are many methods which permit partial rejection of biological background. Alas, without a proper understanding of sources of biological background, a particular step of optimization often negates the results of prior optimization of other parameters. As described in the following, the use of MPD instrumentation permitted better understanding of diverse sources of biological background. This set the stage for the development of a set of methods, which synergistically removes the background and permits the orders of magnitude improvement of sensitivity. This effort had been first accomplished for IA/MPD and more recently extended to Super-ELISA and RGIA.

In the following I disclose the new methods in the development of ultrasensitive immunoassays:
  Testing quality and selection of capture and labeling Abs;
  Preparation of microtiter plates;
  Diminishing cross-reactivity of Abs;
  Blocking and super-stringent washing;
  Optimization of the assay buffer;
  Eliminating the background due to the labeling Abs;
  Eliminating the background due to streptavidin stickiness;
  Techniques allowing use of larger volume of biological sample;
  Use of substrates different than plastic;
  Use of amplification in immunoassays.

In my practice, the combination of a few of such techniques is required to achieve the most sensitive immunoassays.

1. Quality and Selection of Capture and Labeling Abs

In the IA/MPD and Super-ELISA, two separate antibodies are required: one for capture and a second radiolabeled or biotinylated to detect and quantify the captured ligand. Often I use a tracer antibody conjugated with biotin which allows $^{125}$I-streptavidin to be used subsequently. Each antibody pair has to be matched, and no pair can bind to the same epitope.

The literature about sensitive immunoassays almost obsessively focus on the antibodies quality. My experiments documents that the relation between the quality of Abs and the sensitivity of assay is not as simple as suggested by prior art methods. It is true, that one can not perform immunoassays with LOD better than 1 pg/ml without good enough antibodies. However, even with good antibodies, one can improve or diminish the assay sensitivity by at least order of magnitude. In reality, the better antibodies help to reject mainly the biological matrix induced sources of biological background. As I will disclose in the following, other sources of background dominates when all required steps of improvement are used.

Technically, the quality of antibodies is measured by a slope of dilution curves when plotted in appropriate log-log scale. FIG. 25 presents the results for six IA/MPDs for different cytokines. It can be observed that essentially the same sensitivity of 50 zeptomole/ml has been achieved even if slope, ergo specificity, of Abs is very different. FIG. 26 shows that using the same antibodies, very different dilution curves can be obtained. The two curves are for IA/MPD targeting p24, a capsomer of HIV-1. The red curve shows great slope and very good reproducibility, i.e. almost perfect immunoassay down to about 20 fg/ml. However, at about 10 fg/ml a new source of biological background kicks-in and the ability to quantitate is lost. The black curve shows much worse slope but "keeps going" until about 1 fg/ml. The only difference in two assays is that the washing strength has been increased a few fold in each step of assay. It can be seen that signal is lost at higher values of antigen, but the backgrounds are considerably diminished enabling ten-fold improvement of assay sensitivity.

The important step is the selection of antibodies. For example, for cytokines assays I compared Abs from CLB Inc, Amsterdam, Holland and R&D Inc., Minneapolis, USA. The CLB antibodies permit the assay with LOD about three-fold better than the Abs from other suppliers. However when compared at 1 pg/ml, the signal using CLB antibodies is about two-times lower than when using Abs from other commercial sources. Clearly, the CLB antibodies have relatively low avidity but have been selected for increased specificity. Thus, one of the important steps in development of supersensitive immunoassay is to select Abs with highest possible specificity, even if it leads to much lower avidity.

Typically, polyclonal Abs have higher avidity but lower specificity than monoclonal Abs. Prior art immunoassays almost always use the polyclonal Abs as capture Abs and monoclonal Abs as labeling Abs. When developing supersensitive immunoassays with LOD better than 0.1 pg/ml, it is often necessary to use monoclonal Abs as both capture and labeling Abs. This leads to a small loss in signal that has to be countered by the use of more sensitive read-out instrumentation, e.g. MPD or an additional step of amplification.

2. Preparation of Microtiter Plates

We used plastic microtiter plates from four different producers. I documented the advantages of NUNC microtiter plates and subsequently tested about six batches of these microtiter plates.

It is extremely important that covalent binding of Abs to plates does not occur because this leads to drastic increase of background. I stress the need for stringent washing of microtiter plates after coating with Abs. The binding of Abs to plastic is nonspecific and leads to rather wide distribution of forces binding Abs to plastic. Thus, it is advantageous to shake plates when coating. The Abs are then many times bonded to plastic and then removed.

This time dependent process is somewhat similar to binding-dissociation (hoping) processes characteristic for chromatography. It leads to increase of strength of binding over time. However, even in this situation, the majority of Abs is relatively weakly bound to plastic. It is crucial that after the plates are coated, a stringent wash is used. If the stringent wash is not used, the Abs will be removed in subsequent stringent washing steps of immunoassays. My procedure for coating plates is highly counter-intuitive, I put about 10 times more Abs than I need, I make sure that they do not bind too fast and then I strip about 90% of Abs from plate in final ultra-stringent wash procedure. However, these steps are necessary if one wants to reach the assay specificity better than 0.1 pg/ml.

3. Diminishing Cross-Reactivity of Abs

Initially the main source of background was cross-reactivity of Abs. In the following, I often call the capture antibody Ab(1) and the labeling antibody Ab(2). Typical immunoassays were developed for large amounts of proteins, say for detecting ng/ml. To diminish assay deviations from linearity at high level of antigen (Hook effect), prior-art immunoassays use the 105-106 excess of capture antibodies. Thus, traditional immunoassays use up to a few hundred microgram of Abs per well. However, when labeling antibodies are used, there are also used in very large excess 104-105. Thus the Ab(1)-Ab(2) interaction are a priori 108 to 1010 times more probable than Ab(1)-protein-Ab(2) interaction. Obviously, the high specificity of Abs helps. However at 0.1 pg/ml the Abs cross-talk is the dominating source of assay background. Note, that this is a very "specific" background. It has nothing with the biological medium used and is an artifact induced by assay designers tendency to use too high excess of antibodies.

Higher analytical sensitivity of used instrumentation permits to handle low signal if the sources of background are diminished. The probability of creation of Ab(1)-Ab(2) complex is proportional to square of used excess. The most important innovation of the disclosed immunoassays is the use of very small amount of antibodies. I typically use a few microgram of capture Ab per well, i.e. some 10-50 times less than prior art assays. Actually, in some cases I used less than 1 microgram/well. Also, in labeling step I use about 10 times less labeling Abs than prior art assays. Often, I use less than 0.1 microgram of labeling Ab per well. Obviously, this leads to a factor of few diminishment of signal. Use of improved instrumentation, e.g. of MPD permits such loss. However, background is diminished 50-100 times, which leads to a much better signal/background. When antibody cross-reactivity (BAb) was eliminated, diverse sources of background, e.g. due to non-specific interactions of streptavidin became dominant.

4. Blocking and Super-Stringent Washing

Development of innovative blocking reagents permitted about a factor 2-5 improvement of the IA/MPD and Super-ELISA. I tested three families of blocking reagents: caseine based, milk derived and using a specially granulated graphite emulsion. I demonstrated that using the three blockers sequentially provides an advantage in sensitivity providing that a stringent washing is performed between the blocker application. However, due to effort and cost required, I usually use only one blocker, selected according to the nature of targeted protein.

We documented that in case of all blockers, extreme care is necessary that they are highly purified and tested for contamination with biotine.

We demonstrated that for majority of proteins I studied, the blocker based on colloidial graphite works best. It is however important, that the graphite granules are of as small diameter as possible. However, a small fraction (<10%) of larger granules seems to help. Thus I use the mixture of two industrial graphite based ingredients, which are subsequently filtered to remove larger granules and evaluated by microscope.

The washing procedures are extremely important at all stages of the IA/MPD and Super-ELISA performance. The typical washing is performed at the following stages:

w1—30 minutes after overnight Ab(1) incubation;
w2—10 minutes after each blocking step;
w3—30 minutes after incubation with physiologic fluid;
w4—30 minutes after application of Ab(2);
w5—60 minutes after application of streptavidin based reagents.

Note: Washing steps which are crucial for background rejection are underlined.

There is a plurality of good washing methods. Note that I usually perform the washing by hand but the appropriate modalities of use of washing instruments are under development. The different modalities of washing are:

wm1—by a stream of washing buffer manually injected via 8-fold syring manifold;
wm2—by turbulent wash induced by orbital or vibrational shakers;
wm3—by ultrasound wash induced by appropriate ultrasound source;
wm4—by use of magnetic beads rotation induced by appropriate magnetic activator;
wm5—by means of "slow roll" technique.

I note that different methods are working best in different washing steps (w1 through w5). Generally, the strength and length of washing steps is considerably higher in IA/MPD or Super-ELISA than in classical ELISA. I note, that some decrease of stringency of washing steps is possible but must be first carefully designed, implemented and tested for each particular protein target. For example, FIG. 27 shows the Super-ELISA results in which the two washing conditions were used. It is clearly seen that the shorter washing (30 minutes) increases the non-specific biological background by about factor of five.

Advantages of ultrasound washing in higher throughput assay. My current assay is performed in 96 well microtiter plates and is essentially manual. For assay performed in duplicate for up to eight targets, the throughput is low. To facilitate the proposed program of initial clinical studies, I suggest use of 384 well format. This format has an additional advantage in that only 30-40 ul of sample is used per well as compared with 100 ul used in 96 well microtiter plate. In framework of my breast cancer detection project, I performed immunoassays using 384 well plates for all relevant targets (PSA, free PSA, $TNF_{alpha}$, IL-6, IL-8 and VEGF). I observed a considerable increase in non-specific biological background. The sensitivity achieved is about 3-fold less than when using 96 well format. Also, the measurement to measurement uncertainties are larger.

I traced the problem to the insufficient strength of washing. The geometry of wells in 384 well format makes the washing much more difficult. I tried many different washing methods but no progress was achieved. Only recently, I developed an adequate ultrasound-based washing method. The wells are filled with washing buffer and covered with parafilm. Then a strong (>1,000 Watt) ultrasound source with appropriately shaped tip is used to transfer the vibration into well. The 384 well plate is mounted on x-y computer controlled table which permits the homogeneous coverage of all plate surface. The optimization of frequency, power and duration is important. This novel system permitted more stringent and more reproducibly controlled washing than other systems I tried. Using this new ultrasound washing method, I achieved the Super-ELISA for IL-6 with about 50 fg/ml sensitivity in 384 well microtiter plate format (see FIG. 28).

The above described super-stringent washing method permitted another improvement of Super-ELISA. To boost the signal I typically use the streptavidin-poly(HRP). However, the streptavidin-polyHRP is a very large, sticky protein. Previous optimization suggested that streptavidin-HRP(20) gives the best signal/background ratio. Using my ultrasound-based super-stringent washing procedure, I demonstrated that streptavidin-HRP(80) permits about four times better signal and excellent signal to background.

Our experiments with this new method of ultrastringent washing suggest that the higher throughput using 384 well microtiter plates is compatible with better than 0.1 pg/ml sensitivity. This task will optimize these methods and extend them to other biomarkers important in breast cancer detection. These novel methods has been optimized and is being carefully tested for PSA as well as a plurality of cytokines and AFs.

5. Optimization of the Assay Buffer

The assay buffer is an important immunoreagents strongly influencing the immunoassay sensitivity. I found out, that the assay buffer must contain a few percent of proteins per mass. I also documented that the size and other properties of proteins should be distributed over a large range. I found out, that for immunoassays performed above 0.1 pg/ml, the selection of the assay buffer is relatively easy. However for the assay with sensitivity, the different derivatives of Fraction IV of human serum were found to be an excellent assay buffer. However, the said blood derived assay buffer should be tested for contamination with biotine. Typically, I add to such a buffer some components which diminish the probability of cross-talk between $Ab_{capture}$ and $Ab_{label}$, e.g. heterophillic Abs antagonists.

The use of human serum derived assay buffer is especially advantageous when testing for external proteins, e.g. for microbial proteins. FIG. 29 provides an example of IA/MPD for p24 performed in optimized assay buffer and in assay buffer recommended by another group. All other assay conditions were identical. Note that a factor of 5 to 10 improvement is achieved when optimal assay buffer is used.

However, when the targeted proteins are natural molecules present in human blood, e.g. cytokines, PSA or tau protein, the use of human serum derived components of assay buffer leads to artifacts. Thus, I developed the assay buffer based on serum of animals from another branches of evolutionary tree. Note that as the majority of Abs are produced in mouse or rabbit. As such, the serums must be from animals evolutionarily distant from humans, rabbit and mouse. Therefore, I studied the assay buffers based on the sera of birds, reptiles and fish. I found the best but also the most costly assay buffer was developed from snake serum. However, the alligator serum, fish roe and other proteins obtained from fish appear to work well. The serum of domesticated birds has been tested—the commercially available serum of chicken is not good but serum of ducks, goose or turkey is promising. I compared immunoassays performed using chicken and snake serum with all other assay conditions invariant; the assay using snake serum is much better.

6. Eliminating the Background Due to the Labeling Abs

The cross-talk between Abs is a most important limit on immunoassays sensitivity. When using a typical Abs excess as recommended in prior-art immunoassays, the cross-talk limits the assay sensitivity at about 0.1-0.5 pg/ml. This limit varies for different target protein and depends on quality of used Abs. The cross-talk is highest when both Abs are polyclonal, is manageable when using an appropriate set and excess of both poly-Ab and mono-Ab. Usually it is lowest when using two different m-Abs but this may lead to very low signal. I diminished the background due to cross-talk by using a very low amount of labeling Abs, typically about 0.1 microgram per well.

Because of the use of very low amount of labeling Abs, the equivalent background is around 10 fg/ml. It can be further diminished by use of:

Highly turbulent medium, e.g by means of shaker during incubation phase;

Shortening of incubation time to be less than 30 minutes;

Optimal pH and temperature, e.g. other than pH 7.0 and Temp 27° C.

As mentioned above, the very stringent washing is important after Ablabel incubation.

7. Eliminating the Background Due to Streptavidin Stickiness

There are many putative advantages of using the larger constructs as labeling reagent in IA/MPD and Super-ELISA. Series of experiments suggest that currently the dominating source of background is stickiness of streptavidin. The use of $^{125}I$- streptavidin vs. Streptavidin-HRP vs. Streptavidin-polyHRP, is discussed below.

First, up to one hundred $^{125}I$ can be placed on a single molecule, thus leading to a much shorter read-out time in supersensitive IA/MPD and P-chips/MPD applications. Second, it is expected that even in large complexes, the "stickiness" is mainly from streptavidin. However, the washing forces are much larger. Thus, with streptavidin-PolyHRP a much more stringent wash can be implemented leading to lower background.

Beyond Streptavidin-$^{125}$I: An innovative multi-iodinated strep-reagent is based on streptavidin-poly-tyrosine which is a tetramer. I disclose the use of a modified molecule in which each monomer has at least five added tyrosine residues. Subsequently, these tyrosine residues were radiolabeled yielding relatively small, but multilabeled, reagents. Each streptavidin molecule, consisting of four subunits, contains 24 Tyr residues, but these Tyr residues have limited accessibility. Thus, streptavidin, labeled with $^{125}$I using Chloramine T and iodogen methods, has relatively low specific activity. Similarly, streptavidin, labeled with $^{125}$I using Bolton-Hunter reagents, has low specific activities, due to the limited accessibility of primary amino groups. If additional, accessible Tyr residues could be introduced into streptavidin, the resulting streptavidin derivative could be labeled with $^{125}$I at higher specific activities. I produced streptavidin derivatives containing poly-Tyr sequences, Stv-(Tyr)$_n$. An expression vector for streptavidin-containing chimeric proteins, pTSA-18F was used as the platform. This expression vector carries the core streptavidin gene with a polylinker sequence under the control of a bacteriophage T7 promoter. Thus, gene fusions of streptavidin with any partner proteins can be constructed. I inserted an oligonucleotide encoding a (Tyr)$_n$ sequence into the polycloning site of pTSA-18F. The number of Tyr residues (n) in each (Tyr)$_n$ sequence was set at 5, 10, or 20. Thus, the number of Tyr residues in each tetrameric molecule is 20, 40, or 80, respectively. Each of these gene fusions, which encodes streptavidin with a (Tyr)$_n$ sequence at the C-terminus, will be expressed in *E. coli* and purified. Purified Stv-(Tyr)$_n$ constructs could be labeled with $^{125}$I at high specific activities using an Iodo-Beads iodination reagent. However, fusion of (Tyr)$_n$ sequences to the C-terminus of streptavidin might disturb the folding and tetramer formation. I successfully created Stv-(Tyr)$_5$. I initiated the R&D program to determine experimentally whether longer (Tyr)$_n$ sequences (n=10 and 20) would affect the folding and tetramer formation of streptavidin.

The streptavidin was used in a solution at 38 ug/ml. To achieve the low specific activity iodination I used the following procedure. To 20 ul of this solution (ca. 0.76 ug) there was added 2 ul of pH 7.4, 0.1 M phosphate buffer and 0.5 ul of Na$^{125}$Isolution (ca. 0.2 mCi). After mixing, 10 ul of 1.0 mM Chloramine T solution was added and mixed for 1 min. The reaction was allowed to proceed for 5 min and was terminated by adding 1 mM potassium iodide solution and phosphate buffer containing BSA. The mixture was applied to a Sephadex G-25 column that had been equilibrated with BSA-containing buffer and eluted with the same buffer. The first fraction containing radioactivity was saved and elution continued until free iodide peak eluted from the column. These fractions were disposed of to radioactive waste. The second iodination was performed similarly, but only 10 ul (0.38 ug) of streptavidin and 0.8 mCi of 125I were used. The same procedure was used to purify product, i.e. the second and the first peak of radioactivity to elute from the column was saved. Streptavidin is a tetramer of about 16 kD molecular weight subunits, i.e. a total of 64 kD. Thus, 0.76 ug of streptavidin is roughly 10 pmol and 0.2 mCi $^{125}$I is about 100 pmol, so there are 10 iodine atoms per tetramer in the low specific activity iodination. A typical incorporation ratio is 33 to 50 percent, so there should be roughly 1 iodine atom per subunit or 4 per tetramer incorporated. For the higher specific activity iodination, four times as much iodine and half as much protein were used, so up to 32 iodine atoms per subunit may have been incorporated. Experimentally, radioiodination was between ten and twenty $^{125}$I per molecule level.

Similarly, one could use the streptavidin-PolyHRP and radioiodinate the thyrosines on HRP molecule. With five thyrosine available, the streptavidin-HRP(80) can be labeled with up to 400 atoms of $^{125}$I. However, the full radioiodination is rather difficult to accomplish, and with the radioiodination of half available thyrosine sites the reagent with 200 $^{125}$I can be prepared. The use of such SuperTracer in IA/MPD is disclosed.

Streptavidin-RP vs. Streptavidin-polyP: The main limitation of the Super-ELISA as compared to IA/MPD is about 1,000-fold lower analytical sensitivity of commercial plate compatible colorimeters as compared with MPD Instruments. Thus, in the case of IA/MPD the signal considerations are secondary to ability to diminish the biological background. However, almost all steps leading to background rejection lead to diminishment of signal. Thus, when using colorimeters there is a clear need to amplify the signal. Methods that can be employed to improve the signal include:

Better substrate;
Use of amplification via streptavidin-polyHRP;
Use of second stage of amplification;

I tested a plurality of commercially available HRP sensitive substrates and documented that K-blue substrate from Neopren Inc. is almost always the best and reasonably reproducible.

There are available three types of streptavidin-polyHRP, namely streptavidin-HRP(20), streptavidin-HRP(40) and streptavidin-HRP(80), wherein the number in bracket represent an average number of HRP molecules attached to streptavidin. However, the distribution of molecular masses is rather large. I disclose, the use of centrifugation to improve the distribution of the multiplicity of HRP.

A priori, between the streptavidin-HRP and three streptavidin-HRP(i), i=20,40,80 the signal increase should be by factor 20, 40 and 80, respectively. Alas, the measured signal increase is closer to 8, 12, 16-fold. The major role is played by steric hindrance, but the additional factor is a very stringent wash conditions used. As described above, the stringent wash tends to remove more streptavidin-HRP(I), i=20,40,80 than streptavidin-HRP.

Our results for Super-ELISA targeting TNF$_{alpha}$ suggests that streptavidin-HRP(40) provides the best sensitivity. The signal is best for HRP(80) but the biological background increases. This increase is stronger than increase in the signal. However, for other target proteins, the streptavidin-HRP(20) shows better sensitivity. Thus the use of appropriate streptavidin-polyHRP is an important, target dependent step of optimization. I note, that use of streptavidin-polyHRP is also crucial for ability of using two-steps amplification methods (see following). In this case, use of strept-HRP(20) at both steps seems better than use of larger streptavidin-polyHRP moieties.

We note, however, that the use of streptavidin-polyHRP is advantageous only when using the prior art colorimeters compatible with microtiter format. The development of my proprietary ultra sensitive colorimeter permitted approximately a factor of ten higher instrumental sensitivity. In some cases (example IL-6) the use of StreptavidinHRP seems better than the use of streptavidin-HRP(20). Actually, it seems that the limit of detection using streptavidin-HRP and new, improved colorimeter is at 10 fg/ml. It is comparable with LOD for Super-ELISA achieved when using two-step amplification and prior-art colorimeters.

Short application of Streptavidin based reagents is a key to high assay sensitivity: This background has been considerably diminished by using much shorter time of incubation with $^{125}$I-streptavidin. My experiments with physiological fluids suggest that the NSBB is not yet limiting the sensitivity. It is, however, expected that NSBB will dominate when I improve the sensitivity of my IA/MPD for p24 to the 0.5 fg/ml level.

In both IA/MPD and Super-ELISA background is limited by step using the streptavidin based reagents. FIG. 30 shows the background due to the use of $^{125}$I-streptavidin as function of incubation time, Both the amount of streptavidin an other incubation parameters (shaker, temperature, PH) were already optimized. Note, that the background is clearly proportional to the time of incubation. However, the biotin-streptavidin interactions are much stronger and faster. The full binding is expected to be achieved in a few minutes. However, prior-art assays typically use the 30 minutes incubation time to achieve the maximal signal.

The dependence of assay on the duration of $^{125}$I-streptavidin incubation time is presented in FIG. 31. Clearly, the shortest incubation time of a few minutes enables best sensitivity. However, when incubation time is below 5 minutes, the manual operation starts to lead to some artifacts—the efficient time of incubation is becoming strip dependent. Thus, I usually use the 10 min as 125I-streptavidin incubation time. However, I suggest that this time should be shortened to about 5 minutes when the full automation of assay is possible by means of bio-automatons.

8. Techniques Allowing Use of Larger Volume of Biological Sample

The commercial immunoassays are results of complicated optimization. Trade-off is searched between improved sensitivity, assay reproducibility, short time of performance, assay cost and user-friendliness, e.g. through use of highly automated system. There are essentially two main groups of immunoassays: assays performed in highly specialized automatic "random access" instruments and assays performed in microtiter plates. In the last case, the preferred formats are 96 or 384 wells microtiter plates. The well volume is about 250 microliter and 50 microliter, respectively. Thus, typically one uses 100-150 microliter of biological sample when using 96 wells microtiter plate. The typical volume of biological sample is 25 microliter when using 384 wells microtiter plates. Note, that in majority of biomedical applications, the available sample volume is higher than volume allowed by the well size of selected microtiter plate. I also note, that because of this limitation, the assays developed for 384 wells plates are about four times less sensitive than assays developed for 96 wells plates.

With physiologic samples such as blood or urine available in milliliters quantity, the assay sensitivity can be improved by developing immunoassay techniques, which optimize the biological sample volume used in assay. Different sources of background have different dependence of the geometry of container in which the assay is perform. The sources of background connected with biological matrix are extensive, i.e. are proportional to volume of biological sample. The backgrounds due to nonspecific stickiness of labeling antibody or streptavidin-based reagent are roughly proportional to surface of the container. The background due to cross-talk between antibodies is independent of either volume or surface of used container, i.e. depend only on absolute amount of antibodies use.

The understanding of the relative importance of different sources of biological background has been crucial in my effort of finding optimal volume of used biological sample. It also permitted "rational selection" of shape and surface quality of used containers. For example, no progress in sensitivity by change of volume or surface properties of container has been possible until the "cross-talk" background has been eliminated. I disclose in the following a series of innovative steps which optimizes the volume of used biological material.

Multi-loading based techniques: The simplest optimization uses multiple loading to increase the volume of biological sample. I use here the fact, that amount of capture Abs is in considerable excess over the number of targeted proteins. The molecular mass of capture Abs is 150 kD. Assume that the molecular mass of targeted protein is 20 kD. I typically use 1 microliter of capture Ab per well. However, I estimate that only 10 ng is actually present on the plate after all steps of washing. Thus, if I load 100 microgram of protein with concentration of 1 pg/ml, there is 0.1 pg of protein per well. Thus, using about 10-fold lower amount of capture Ab, the excess is still about 10,000.

Because of different geometrical factors, the single loading of 100 microliter seems to be optimal for 96 wells microtiter plates. However I can load biological sample many times into the same well providing that after each loading a stringent washing is performed. The multi-loading should lead to increased signal but the signal increase may be nonlinear and dependent on concentration of the target protein. In fact, I expect that at larger loading factors, an equivalent of Hook effect, i.e. saturation of signal, may be possible. The experimental studies showed a totally different picture than theoretically expected. I see some signal amplification but it is relatively small at low concentration and become proportional to number of loadings at concentrations larger than 10 pg/ml.

We noted that multi-loading involves many more steps of washing then a single loading. I believe that the specificity of Abs linked to plastic may be considerably changed. The results of multi-loading experiments may be explained, if only a small, say 10% of Abs are retaining their specificity when coated. Thus, the "best" Abs are already occupied during first loading and the subsequent loadings are less efficient due to kinematical considerations. Thus, I developed a strategy in which the time of incubation is increased for each subsequent loading. This helps but only partially.

Overall, the multi-loading only slightly improves the limit of detection (LOD) of supersensitive immunoassay; the background increases proportionally to signal. However, the slope of dilution curves is better when using multi-loading. This leads to improved limit of quantitation (LOQ) and considerably better reproducibility of immunoassay, especially above 0.1 pg/ml.

"Slow Roll" techniques: I disclose a new method of "Slow Roll". This method combines the process of protein capture and wash out in a simple, efficient process. Use of the "Slow Roll" can increase the signal up to three-fold and diminish the background about twice. Also, the sample-to-sample reproducibility improves. The special set of simple mechanical adapters and tools has been developed to enable the user-friendly implementation of "Slow Roll" technique.

The initial experiment was performed using commercially available Teflon tubes that fit tightly into the microtiter plates. The total amount of used biological fluid has been 0.5 ml vs. 0.1 ml, which is my standard in non-modified microtiter plates. In this geometric configuration, the total available volume increased about 5-fold but surface about 10-fold. The 96-wells microtiter plate has been placed on shaker, so that the biological liquid has been thoroughly mixed. The results have been somewhat counter-intuitive: the signal increased only two-fold but the background increased about four-fold. Furthermore, the signal increase has been larger for proteins abundance >1 pg/ml but background roughly constant. The larger surface in contact with biological sample led to a considerable increase of background, even if the adapter tube is not coated with Abs.

The experiment was repeated replacing the Teflon tubes with glass tubes of essentially the same dimensions. Once more 0.5 ml of biological material has been used. The results showed similar increases of signal (2-fold) but the background increased only 1.5 times. Thus the net increase of S/B was about 50% above 1 pg/ml and lower than 20% below 0.1 pg/ml. I interpreted these results as artifacts due to incomplete mixing and washing in this geometrically unfavorable condition.

We realized that commercially available glass vials with diameter of 5 mm and length of about 10 mm fits well a particular set of conical NUNC tubes. Actually, I modified the vials by coating the top of the vial with a thin soft plastic ring. This permitted reliable tightening of connection between the NUNC plate and vials. In practice, I find that using the breakable stripes is more convenient, i.e. in "slow roll" technique I use the 8-wells NUNC strips coupled to eight glass tubular vials.

The use of elongated vials permitted development of "slow roll" technique. Herein, the mixing of biological sample is achieved by slowly rotating all assembly. Note, that the full volume is about 1 ml. However, the mixing is not very reliable when the entire vial is filled with biological sample, e.g. physiologic fluid such as serum. I demonstrated that the optimal filling ratio is from 0.5 to 0.8, i.e. at least 200 microliter is air. The next step has been finding the best rotation speed; I documented that the best results are obtained when this rotation is a few turn per minute. The time of "Slow Roll" has been optimized and is between 10 and 30 minutes depending on targeted protein. Finally, "Asymmetric Slow Roll" has been implemented whereby the assembly rotation is not continuous. The assembly is stopped in position whereby the biological sample is in contact with the NUNC strip for about 30 seconds and then the mixing is initiated again. Thus, there is a much longer period when sample is in contact with Abs and then a high turbulence is induced by fast sample rotation.

We evaluated the "Slow Roll" vs. "Asymmetric Slow Roll" in the immunoassays targeting a plurality of proteins. I concluded that for p24 protein the "asymmetric slow roll" is better but for other targets, e.g. PSA the difference is small.

The immunoassay for TNF-alpha has been implemented in both normal configuration and using "Slow Roll" technique. The results are presented in FIG. 32. Note that "Slow Roll" permits sensitivity improvement by a factor of about five. Also, the slope of curve is better which improves the measurement reproducibility. I believe that the "slow roll" is an important new technique because it implements a situation wherein the Abs capture is immediately followed by stringent, turbulent washing which considerably decreases the biological background. Thus, "Slow Roll" can be used in any stage of immunoassay, both for capture of targeted protein, in incubation of Ablabel and when using streptavidin-PolyHRP.

We note, however, that "Slow Roll" requires a considerable amount of material-typically 0.5-0.7 ml per measurement. Thus, I suggest that it is especially advantageous when relatively large amount of material is available, e.g. urine or breath condensate. Also, it is suggested for use with environmental samples, which are usually available in 50-100 ml quantities.

Microscopic beads based techniques: The further extension of the use of granulated substrate is when using micron-sized beads. Because of general difficulty of separating such microscopic objects, probably the most elegant is the use of micron sized, magnetic beads. Because of diffusion limits, the detection of material below attomole/sample level is difficult. Using the magnetic beads, I achieved the similar sensitivity as using microtiter plates but achieved a factor of few faster assay. More specifically, the steps of washing are considerably improved when the substrate beads are "locked" in rotating magnetic field. In a sense, the use of micron size magnetic beads permits another implementation of a process in which there is a multi-cycle sequence of target protein immobilization and washing. Thus, in a sense this permits another implementation of "Slow Roll".

Macroscopic beads based techniques: Another method for measuring the large volume of material is to use microscopic beads with diameter from 0.5 to about 3 mm. A plurality of this size beads is commercially available including different types of glass and plastics, e.g. polypropylene and Teflon. The metal beads, or metal-coated beads are also available, including beads covered with silver and gold. I developed the sensitive immunoassays, wherein the beads are coated with Abs and then processed inside of glass vials. The use of macroscopic beads has many advantages:

Good size distribution and excellent sphericity;
Availability of beads made out of many different material;
Ease of "fine tailoring" the surface to change its fractal properties and thus modify the amount of Abs which can be loaded;
Excellent kinetics and ability to wash the beads very well;
Ability to concentrate the sample by gravity sedimentation, filtering or magnetically removing the beads.

Another advantage is to use the library of beads coated with different Abs. Such library can be "coded" by any of the following parameters: color, magnetic permeability, size or sphericity. This property permits to develop a panel of immunoassays, which is performed using a single sample of physiologic fluid.

The microcapillary as immunoassay substrate: preferred implementation of RGIA technique. As disclosed above, the use of reverse geometry improves the sensitivity of immunoassays. The main element enabling RGIA is availability of mass-produced pins with well defined geometries and well understood material properties, i.e. well defined interactions of proteins with the pins. Such pin collections exists in a format compatible with 96-well microtiter plates, but not in a format compatible with 384-well microtiter plates. Because of geometric limitations, the pins with a diameter smaller than 2 mm and length of 0.5-1 cm are of interest. I evaluated a few types of existing pins, either glass, plastic or metal-based. Generally, glass pins have too small protein binding power. The plastic made or plastic covered pins are typically not homogenious leading to big jitter in quantitation. The metal coated pins, with exception of gold coated pins, are too active chemically leading, to artifacts in interactions with biomolecules.

We found that the excellent implementation is the use of the glass microcapillary coated with about 50 microns of mylar. These are mass produced, low cost/high reproducibility objects used in blood banking practice. I demonstrated that they have favorable Abs binding properties and are an ideal surface for RGIA. I implemented the RGIA technology based on mylar-coated glass microcapilary which is compatible with the 384-well microtiter plate format.

9. Use of Substrates Different than Plastic

As described above, the current limiting factor is a non-specific sticking of labeling Abs, especially streptavidin based reagents to the surface of plastic. I achieved a landmark 1 fg/ml sensitivity for IA/MPD because I spent a very long time analyzing and selecting best surfaces and then using best methods for blocking and washing. The majority of these efforts have been spent on commercially available microtiter plates with my best results using the NUNC microtiter plates.

The smoothness and fractal properties of surface on which the capture Abs are deposed plays important role in development of supersensitive immunoassays. Thus, I studied many types of surfaces trying to understand the influence of surface chemical and physical properties on assay sensitivity. I note, that for different surfaces, new methods of blocking and washing may be necessary. Initial series of experiments has been with different plastics. For example, I developed the method of conjugation of capture Abs to Teflon surface. A factor two better wash can be obtained when using Teflon and the "shock wave" cleaning. The methods of coating the Teflon with Abs have been developed. Subsequently I studied other surfaces as well.

We also studied the process of binding $^{125}$I-Abs and $^{125}$I-streptavidin to the surface of glass coated by Gold, Silver and Copper. The dynamics of coating and washing of metal coated surfaces seems to be similar to the "fractal" surfaces, but much higher coating can be obtained.

Many groups use the magnetic beads in immunodiagnostics. Magnetic beads have many advantages when fast and sensitive assays are to be developed, because the efficient mixing and separation can be obtained. Thus, I studied the background properties of different magnetic materials. I tested micron-sized magnetic beads from Dynal and other producers. I also studied the properties of rare earth sintered magnets as well as the "gummi" filled with micron-sized magnetic powder. All these magnetic materials have high binding power characteristic for "fractal" surfaces. However, I also studied properties of optically polished hematite and documented that it is a material with lowest known non-specific background due to proteins adsorption: it is about twice better than glass and five times better than Teflon.

We documented that binding power of surface vary by a factor fifty (50). Plastic and glass are not the best surfaces. However, they are the easiest to produce in high quantity. The important findings of different properties of surfaces are provided in Table 4. The protein adsorption per unit of surface has been measured using $^{125}$I-Abs and $^{125}$I-streptavidin for 1 hour in water solution, pH=7 at room temperature. It has been normalized to adsorption by NUNC plates per square mm of surface. Note, that about factor 100 dynamic scale of loading between metal magnetic beads and hematite surface. The error in measurement is less than 20%. When highly granulated material is used, father factor ten seems possible, but grains size distribution, ellipticity and surface properties are variable. The batch-to-batch variability is about 50%.

TABLE 4

Properties of tested surfaces.

| Type of surface | Treatment | Abs absorption | Reproducibility | Wash |
|---|---|---|---|---|
| Metals: | | | | |
| Ag | None | 10 | Good | *** |
| Au | None | 5 | Good | *** |
| Cu | None | 3-5 | Fair | ** |
| | I) NaOH | 5-6 | Good | *** |
| | II) HF | 5-6 | Good | **** |
| Plastics: | | | | |
| NUNC Microsorb | Optical Polish | 1 | Very Good | *** |

TABLE 4-continued

Properties of tested surfaces.

| Type of surface | Treatment | Abs absorption | Reproducibility | Wash |
|---|---|---|---|---|
| | III) Sand blasting | 2 | Good | *** |
| | IV) NaOH | 2 | Fair | *** |
| | V) HF | 1.5 | Good | *** |
| Polyester | Optical Polish | 0.5 | Good | **** |
| | VI) Sand blasting | 1 | Low | ** |
| | VII) NaOH | 0.75 | Fair | *** |
| | VIII) HF | 0.75 | Fair | ** |
| Teflon | Optical Polish | 0.3 | Good | **** |
| | IX) Sand blasting | 0.5 | Low | ** |
| | X) NaOH | 0.4 | Good | *** |
| | XI) HF | 0.3 | Fair | ** |
| Glasses: | | | | |
| Lime | Optical Polish | 0.2 | Fair | ***** |
| | XII) Sand blasting | 0.3 | Low | **** |
| | XIII) NaOH | 0.3 | Fair | **** |
| | XIV) HF | 0.3 | Fair | *** |
| Borosilicate | Optical Polish | 0.2 | Fair | ***** |
| Magnetic: | | | | |
| Dynal 1 microns | Tosyl | 20-30 | Low | ** |
| Dynal 3 microns | Tosyl | 10-20 | Low | ** |
| Cobalt (Sintered) | None | 5-10 | Low | * |
| Magnetic Gummi | None | 0.5 | Fair | *** |
| Hematite | Optical Polish | 0.1 | Very Good | ***** |

Our studies provided a large body of new information about the properties of different substrates. From this information I can project their applicability to supersensitive immunoassays, e.g. their relation to background limited sensitivity. Unfortunately, there seems to be a clear trade-off between the ability to bind Abs and non-specific biologic background. For glass, the background is extremely low but density of captured Abs low. Thus glass can be used only in configuration when large surface is achievable, e.g. when granulated.

We showed that some compromise could be achieved by physical-derivation. Furthermore, I disclose new, innovative direction. I developed the concept of variable, magnetically coupled "beads on glass" (BOG) concept.

We should point out that immunodiagnostics could be implemented with any of the above described surfaces. However, when the enzymatic labels are used, e.g. HRP, the chemical properties of used surface should be taken in account. I demonstrated that when using the colorimetric read-out the metals and hematite interact with color forming substrate. The only exception seems to be gold. Thus, they cannot be used in Super-ELISA. Additionally, some technical plastics seem to interact with color changing substrate, most probably due to impurities. However, pure plastics including Teflon work fine.

Different Methods of Derivatizing Glass as Substrate for Sandwich Assay

Reproducible capture of proteins on surface of glass or plastic can be obtained under two very different conditions. In the first case, the optically polished glass or plastic is used. The binding power of surface is low but high level of reproducibility can be achieved. The binding power seems to be roughly proportional to the incubation time. Also, the washing process is reasonably predictable—the fraction of proteins washed out is roughly proportional to washing time. At the 2nd case, the surface of glass/plastic is either mechanically (sand dusting) or chemically modified to obtain rich fractal surface. The reproducible loading power about 2-5 times better than for polished surface is obtained. However, the amount of protein captured on such surfaces is not a linear function of time. After some time "saturation" is observed, i.e. there seems to be a characteristic "maximal binding power" of such highly disordered, fractal surfaces. Also, the wash out seems to be a much more complicated process in the case of "fractal" surfaces versus that seen in the optically polished surfaces. Both the speed and linearity of wash is quite dependent on the details of process by which fractal process is obtained.

Use of glass leads to a further improvement of background. When using very stringent wash procedure, about 5-fold smaller background has been observed in glass than in NUNC microtiter plates. The main challenge of using glass is the lack of a reliable procedure for coating with Abs. The two possibilities are: chemically derivatize the glass or change the fractal properties of the glass. I disclose silinization of glass. I performed a series of pilot experiments in which the surface of glass was modified. I studied three methods: abrasion of the surface by mechanical means, abrasion of the surface by impact (sand dusting) and modification of the surface by chemical etching (with hydrofluoric acid or with concentrated NaOH). In the "glass on glass" (GOG) technique, the modification of fractal structure of surface is used to optimize the glass binding properties. The mechanical abrasion gives good results but is expensive. Abrasion of the surface by impact (sand dusting) increases the amount of captured Abs about 10-fold providing a longer incubation time. The stickiness of streptavidin increases but only about two-fold. Thus, improvement in the S/B ratio by a factor of five seems possible. It is a low cost method and may allow fully automatic production of hundreds of glass surfaces in parallel. It may be especially useful for supersensitive immunodiagnostics. The glass etching provides the low cost method for modifying the surface properties of glass. I used both concentrated and diluted (20%) hydrofluoric acid. An overnight etch seems necessary in room temperature, but this time may be considerably decreased when operating at higher temperature. The capability to capture Abs has been increased by a factor of a few. I tested etching with concentrated NaOH; the results seem to be slightly better than with acid. The limitation of the "etch" method is that the method induced some jitter in the amount of captured Abs. I traced the problem to the existence of spots of grease on commercially produced glass. The repetitive stringent washes diminish the jitter.

10. Use of Amplification in Immunoassays

MPD is not technically a radioactive method; less radioactivity is used than is contained in cup of coffee. However, in many applications it would be better to use other read-out method. I are interested in the super-sensitive methods of protein quantitation, i.e. in proteins quantitation at the sub-attomole/ml level. For a typical protein with a 20 kD molecular weight, this translate into 0.05 pg/ml level, i.e. about 50 times better sensitivity than the current generation of immunoassays. At this sensitivity level, existing immunoassays are limited by different sources of biological background and low signals below the analytical sensitivity of read-out devices. There are important system non-linearities, i.e. it is almost impossible to quantitate below 0.1 pg/ml.

Practically, there are two main methods; improve the analytical sensitivity of read-out device or amplify the signal. In IA/MPD I selected the first option. I developed the detector, which is about 1,000-fold sensitive than typical colorimetric plate readers. This permitted us to better understand the sources of biological noises and remove them by changes in biological procedures. As documented above, in my IA/MPD assays the level of non-specific biological background is at about 1 fg/ml. These proprietary methods of biological background reduction permit us to initiate the search for better methods of signal amplification.

There are many methods of signal amplifications for proteins, but only a few are compatible with ultrasensitive immunoassays. For example, a classical method of amplification is the ELISA itself. In this case, amplification is achieved through the high processivity of the used enzyme, e.g. HRP. In newer implementations, streptavidin-polyHRP is used to achieve further signal gains. Strep-polyHRP(n) is available from several commercial suppliers, where n=20,40 and 80 is average number of HRP per streptavidin. In development of Super-ELISA I tested all available strep-polyHRP. I observed that due to the steric hindrance the signal gain is much less than suggested by the HRP multiplicity, i.e. the gain when using streptavidin-HRP(80) is only about 15 fold, i.e. factor 5 lower than maximal gain of signal calculated from stoichiometry.

The amplified IA/MPD and Super-ELISA: It is important to understand all sources of background when using a particular streptavidin based reagent. From a series of experiments, I concluded that in:
  IA/MPD the background is dominated by the nonspecific sticking of $^{125}$I-streptavidin to plastic
  Classical ELISA using streptavidin-HRP(1), the background is due to instrumental background
  Super-ELISA using streptavidin-HRP(20) the background is still due to instrumental background but a detectable fraction of background is due to streptavidin-HRP(20)
  Super-ELISA using streptavidin-HRP(80) the background starts to be dominated by non-specific sticking of label to plastic, but can be significantly diminished by super-stringent wash.

I noted that streptavidin-HRP(i), i=1, 10, 20, 40, 80 are very large molecules which for i>10 with molecular mass in excess of 1 MegaDalton. However, the non-specific binding to plastic is still mostly by one or two "contact places". The large cross-section of the molecule means, that stringent washing may break a non-specific ergo weak plastic-streptavidin-polyHRP binding but not a strong, biotin-streptavidin-polyHRP binding. Super-stringent washing can be efficient with removing the background due to non-specific sticking of streptavidin-polyHRP to plastic. It will lead to some signal reduction, but this is easily compensated by amplification available with streptavidin-polyHRP.

My studies permitted a partial understanding of the complicated interplay between signal and background when streptavidin-polyHRP is used as label; the factor of ten signal gain and a factor of few gain in signal/background seems possible. Thus, I implemented two types of amplified IA/MPD. In the 1 st case, I use streptavidin-polyHRP(20) followed by stringent wash and application of anti-HRP antibody labeled with $^{125}$I (see FIG. 33). The good anti-HRP monoclonal antibodies are commercially available. For example, both mAbs and biotinylated mAbs are available from Jackson Immunological Laboratories, East Grove, IL. Radio-iodinated anti-HRP Abs are not available, and I developed the amplified IA/MPD wherein the (antiHRP-biotin)-($^{125}$Istreptavidin) complex is used. This assay, shows comparable sensitivity with IA/MPD but is a factor of about ten faster, i.e. at sub-0.1 pg/ml level requires a shorter counting time to achieve the sufficient statistics of $^{125}$I decays. Note, that using these two steps of amplification I achieved the similar gain of signal as when using the multi-iodinated streptavidin, e.g. multi-iodinated streptavidin-polyHRP, wherein each HRP is iodinated. I also developed the streptavidin-Tyr(20), wherein each tyrosine may be radio iodinated. My results are still quite preliminary, but there is no much difference between all these amplified IA/MPD. The user convenience and cost of reagents will decide.

Based on the amplified IA/MPD, I designed the amplified Super-ELISA (see FIG. 34). In Super-ELISA, after the conjugation of streptavidin-HRP(20), the appropriate substrate is provided leading to the change of color measured by colorimetric plate reader. In amplified Super-ELISA an additional step of amplification is performed. I use the biotinylated anti-HRP monoclonal antibody in about 10,000-fold excess (we always calculate the excess at the pg/ml value and per HRP). Thus for 10 fg/ml the excess is much smaller—only hundred-fold per each HRP present. The incubation time of about 10 minutes is sufficient to allow the interaction of anti-HRP with about 50% of HRP at the system. Subsequently, after stringent washing, the fresh streptavidin-HRP (20) is applied in excess. Also in 2nd amplification step, I used the excess factor of 10,000 of streptavidin-HRP(20) over the number of biotines available at 1 pg/ml. Following stringent wash, the color creating substrate is provided and the color change is measured using commercial colorimetric plate reader.

This two step amplification method achieved about 100-fold signal amplification as compared with use of streptavidin-HRP(1). My results suggest that when using streptavidin-HRP(20), each step of amplification leads to about a ten-fold signal amplification but the background is dominated by the first step of amplification. A relatively low amplification per step leads to reasonable linearity, robust assay which achieved a landmark 5-10 fg/ml sensitivity. FIG. 35 documents supersensitive immunoassays for $TNF_{alpha}$. It shows amplified Super-ELISA using "slow roll" and two stages of amplification with streptavidin-HRP(20). Note that each step of amplification leads to about a factor five gain in sensitivity as demonstrated by the achieved limits of detection (LOD) of 100 fg/ml, 20 fg/ml and 5 fg/ml, respectively. More importantly, these improvements "pile-up", leading to amplified Super-ELISA with excellent reproducibility (CV=20%) down to 10 fg/ml.

We believe that the proposed "two step amplification" scheme is very promising. The advantages are:
  *Amplified Super-ELISA provide 100 fold improvement of sensitivity as compared with best "classical" ELISA using streptavidin-HRP(1)
  All reagents are available commercially from a plurality of sources and at low cost
  The method is compatible with available equipment, e.g. 96 or 384 wells microplate automatic liquid handlers, plate washers and colorimetric plate readers;
  Further improvements are possible.

Use of amplification in RGIA: RGIA uses millimeter diameter "pins" and available surface for Abs binding that is smaller than the surface of the wells in a 96 - or 384 -wells microtiter plate. This leads to a signal substantially lower than the signal in ELISA or Super-ELISA. In RGIA, the streptavidin-HRP should be replaced with streptavidin-polyHRP. This is a direct amplification method. HRP(20) is typically used to bring the signal above the analytical sensitivity level of calorimeters. However, use of a much larger labeling molecule (2 MegaDalton vs. 60 kiloDalton) leads to a considerable increase in NSBB.

The performance of RGIA can be improved by using a two-step amplification method. In the first step, streptavidin-HRP(20) is used which binds to biotinylated Abs. Good anti-HRP monoclonal antibodies are commercially available. For example, both mAbs and biotinylated mAbs are available from Jackson Immunological Laboratories, East Grove, Ill. In the second step this anti-HRP Abs are used. Finally, streptavidin-HRP(20) is used in about 100-fold excess. It is crucial to control the excess of both ant-HRP and streptavidin-HRP (20) at all relevant steps. I observed that a signal gain by a factor 10-20 can be achieved with only 2-3 fold increase of background. Thus, the signal/background ratio is improved about 10 fold. This permits us to compensate for the intrinsically low signal of RGIA method.

Biomedical Applications

We disclose here three applications in which the IA/MPD and Super-ELISA demonstrated considerable advantages in biomedical diagnostics.

Applications of Immunodiagnostics in Oncology: The NIH estimates the overall costs for cancer in the year 2001 at $156.7 billion; $56.4 billion for all health expenditures, $15.6 billion for the cost of lost productivity due to illness, $84.7 billion for the cost of lost productivity due to premature death. (ACS, "Cancer Facts & FIGS. 2002," (2002: 3-15).

What is needed is the ability to assay many markers and to develop an accurate correlation between the presence of the markers and the presence of the tumor. The challenge of specificity needs to be addressed. I proposed the use of the supersensitive MultiPhoton Detection (MPD) techniques coupled to ImmunoAssays (IA/MPD) and Protein-chips/MPD to detect tumor markers in concentration ranges from 0.01 pg/ml level to 500 pg/ml. I actually extended this supersensitive technique to a more user-friendly Super-ELISA and Reverse Geometry Immunoassays (RGIA). These technologies resulted in a more sensitive and specific diagnostic method, which in pilot studies enabled the reliable detection of the tumors in an earlier stage of development.

Breast cancer: Breast cancer is the most common form of cancer among women in the United States. In 2003, the American Cancer Society estimates that more than 210,000 new cases of breast cancer will be diagnosed and that approximately 40,000 will die of the disease. In recent years breast cancer mortality rates have declined significantly. The decrease is a result of both earlier detection and improved treatment. The five-year survival rate for breast cancer is about 97% when the cancer has not spread at the time of diagnosis. Thus, early detection is very important. The new treatment modalities, especially new combination therapy, are very promising. However, reliable means for prognosis and therapy monitoring are still missing.

The guidelines in the United States for women set forth by the American Cancer Society [ACS]) are:
  Clinical breast exams should be part of periodic health examination, about every three years for women in their 20's and 30's, and each year for women 40 years and over
  Yearly mammograms starting at age 40
  Women with increased risk for breast cancer due to family history/genetic tendencies should consider starting mammography screening earlier and possibly with higher frequency Trials have repeatedly and convincingly confirmed that breast cancer is a progressive rather than systematic disease. Progression of breast cancer can be arrested through detection and treatment at an early stage. The time at which disease progression is arrested has significant impact on clinical outcome. Thus, early diagnostics, including mammographic screening, are key factors in the control of breast cancer. Roughly half of these newly diagnosed patients are node negative, in which case therapy is more effective. However, about 30% of these cases still progress to metastatic disease.

Physical examination, mammography, ultrasonography and fine needle aspiration are used in breast cancer diagnosis. The triple test score (TTS) integrates physical examination, mammography and fine needle aspiration in the evaluation. The cost is currently about $400 for mammography and about $600 for TTS. However, cost per malignancy discovered is about $2,000-3,000 due to need of open breast biopsy. More comprehensive testing may considerably diminish the need for open biopsy. Mammography remains the diagnostic test of choice for breast cancer, even though 20% of cancers may go undetected. Many serum biomarkers have been reported but no single biomarker present in blood has proven effective. I demonstrated that the level of PSA in women serum is a very promising early marker. Thus, the search for new biomarkers and the use of biomarker panels was necessary. For example, women age 70 and older have the highest incidence and mortality from breast cancer. Barriers to routine mammography of older women are many, and in this population blood based tests performed at home will be especially important.

Early discovery of breast cancer facilitates effective therapy. There is, however, much heterogeneity in the survival of breast cancer patients. Patients with favorable characteristics have significantly longer survival. There are numerous reports on predictive and prognostic factors and their correlation with response time, time to progression and overall survival. The factors that have been shown to be predictive of response in patients receiving hormone therapy are receptor status, dominant site of metastasis and menopausal status. Also, age, number of metastatic sites, and performance status have been suggested as prognostic factors.

PSA coupled with the anti-inflammatory cytokines $TNF_{alpha}$ and IL-6 and the AFs IL-8 and VEGF have been used to establish a panel of promising biomarkers for the detection of breast cancer creating the possibility of an easy to perform/low cost blood based screening assay based on measurement of PSA, $TNF_{alpha}$, IL-6, IL-8 and VEGF levels in the serum of women. I will further improve IA/MPD and Super-ELISA targeting "free" and "total" PSA with LOD of about 10 fg/ml. This is a hundred-fold more sensitive than current ELISA assays. Thus, clinicians will have an economical, sensitive, selective diagnostic assay to correlate an extended set of biomarkers with the presence of tumors.

Supersensitive assay for PSA and its applications in oncology: Introduction of the PSA test in the late 1980's detected many otherwise inapparent tumors. In men, PSA is produced mainly, but not exclusively, by the prostate, and its blood levels are much higher in men than in women. PSA is also known to be produced by breast tissue in women.

PSA is a single chain chymotrypsin like, serine protease and is a member of the kallikrein family. PSA is synthesized by epithelial cells lining the acini and ducts of the prostate gland. It is then secreted into the prostatic ducts and is present in seminal fluid. Since PSA in blood is produced by the normal prostate, as well as by prostate tumors, reliance on high PSA levels alone for diagnosis leads to many false positives.

The first generation of PSA assays had sensitivity of about 50 pg/ml, and the current assays are at LOD of about 5 pg/ml. I developed three types of supersensitive immunoassays targeting PSA,(IA/MPD, RGIA and Super-ELISA) which achieved the 10, 20 and 50 fg/ml sensitivity, respectively. The performances of Super-ELISA are presented in FIG. 36. I also documented excellent reproducibility (see FIG. 37). I used this new assay to measure the level of PSA in plasma samples from 50 healthy male blood donors. Because of superior sensitivity, I diluted the said plasma samples 1:10 with assay buffer. Even after this dilution, I could reliably quantitate the PSA level in all samples. Measurement is fully quantitative both for very low and very high values of PSA; I observed a very large dynamic range from about 0.2 pg/ml to about 10 ng/ml. I observed good agreement with measurements using commercially available immunoassays for PSA.

We measured the 75 samples of serum from patients after radical prostatectomy. The samples were obtained during the routine check-up, six months after operation. As expected, the level of PSA in majority of man after prostatectomy the level is very low, down to 30 fg/ml. Actually about 70% of patients have level below 1 pg/ml and are immeasurable with the prior-art assays. However, for about ten of 75 patients the level is somewhat higher, from 5 to 10 p/ml. These patients are interpreted as the ones with putative metastasis. I suggest that for all patients with above 1 pg/ml, one should perform the "PSA velocity" measurements.

PSA for breast cancer diagnostics: PSA has been found in various female tissues and body fluids. Female breast, both normal and cancerous, produces PSA, and this production is regulated by estrogen and progesterone. Preliminary data suggest that women with breast cancer may have a better prognosis if the level of PSA in tumors is high. A seminal study examining the prognostic value of PSA in a large cohort of US patients, using an assay with a few pg/ml detection limit, measured the level of PSA in tumor cytosolic extract of 953 women with preliminary breast cancer diagnosis. Detectable PSA, i.e. PSA level >2-3 pg/ml was found to be significantly associated with: smaller tumors, tumors with a small s-phase fraction, diploid tumors, younger age, and tumors with lower cellularity. Due to the need for breast extracts and the relatively low sensitivity of the current generation of immunoassays for PSA, these studies could not be extended to PSA based early diagnostics of breast cancer. The development by my group of the immunoassays for PSA with about 100-fold better sensitivity enabled the preliminary studies of level of PSA in blood of healthy women and breast cancer patients. The initial results are described in the following.

We studied three sets of serum samples from healthy women. The first set of thirty came from primarily young, women (from 20-50 age) who were blood donors at Hospital Charite, Berlin, Germany. The second set came from thirty middle aged American women (age 40-60 years). The third set came from thirty older women (age 60-90 years). The last two sets were acquired from Impath Inc., CA., USA. The overall age distribution of available samples of healthy women is between 20 and 90 years. The distribution of PSA levels for all 88 samples is presented in FIG. 38; the range is from 0.1 pg/ml to about 2 pg/ml, with about 15% of women showing higher levels of PSA up to about 5 pg/ml. The distribution is relatively well fit by a Gaussian with a tail at higher PSA levels. When the PSA distribution is compared to distribution of each set, one observes a clear dependence of PSA level on age. I performed a statistical analysis of the dependence of PSA level on age. The data are well fitted ($R=0.971$) by the functional dependence $y=a+bt^3$, where y is the average level of PSA and t is average age in the given age bracket. Observe that the average level of PSA rises monotonically with age, first slowly (up to 60 years) and then much faster for older women.

We studied a set of serum samples from women with non-treated breast cancer (NT-breast cancer). These sample sets were acquired from Impath Inc., CA., USA. The overall age distribution of available samples of NT-breast cancer women is from 20 to about 80 years with most ranging from 50 to 70 years of age. The distribution of PSA levels for these 48 samples is from 0.1 pg/ml to about 10 pg/ml, with about 15% of women showing much higher levels of PSA up to 100 pg/ml. The distribution is bi-modal, with about 40% of low PSA samples compatible with Gaussian with a tail at much higher PSA levels that can not be fitted by any curve I tried. It is clear that the level of PSA in many NT-breast cancer samples is much higher than in samples from healthy women. However, taking into account the somewhat different age distribution of these two cohorts, a more correct way to compare them is by using the age-adjusted level of PSA as described above. The comparison of the two distributions after taking into account the age dependence is confirms large differences in distribution. The frequency of women with z>z cut-off is presented for the said two cohorts. Here, z is the age-adjusted level of PSA. After appropriate integration, two very different distributions are obtained for NT-breast cancer and healthy women. It can be seen that for z>2 there are about 60% of women with NT-breast cancer but only 16% of healthy women. For z>3 there are about 50% of women with NT-breast cancer but only about 10% of normal women. The ratio of probabilities for PSA level with z>z cut-off is illustrated in FIG. 39. This is a smoothly rising curve with a maximum of about 8 at z>5. I note that the rather low number of samples from women with NT-breast cancer does not permit extrapolating the curve to even higher values of z cut-off.

The results described above strongly suggest that there is a significant difference in the distribution of serum PSA levels in women with non-treated breast cancer and healthy women: the level of PSA in serum of women with cancer is higher than that in healthy women. However, in women whose breast cancer was treated, the level of PSA is lower and the age dependence is different. This suggests the possibility of using the age-adjusted distribution of PSA as screening biomarker.

Applications of supersensitive diagnostics proteomics in detection of breast cancer: Breast cancer is the most common form of cancer among women in the United States. Consequently, there is an increasing need for better diagnostics. New markers/methods may permit more reliable, early detection prognosis and therapy monitoring of breast cancer. Thus, blood-based tests may be complementary to mammography.

We measured 159 samples of serum from two cohorts of women with untreated breast cancer. Information about the menopausal status of the women with breast cancer is not available, but taking into account the age distribution, about 30% of them are expected to be post-menopausal women. I measured PSA, $TNF_{alpha}$, IL-6, IL-8 and VEGF for all samples. For some samples also $IL-1_{beta}$ and IL-4 was measured. Overall, I have studied 159 samples classified as putative breast cancer based on mammography and 107 samples for which both mammography and biopsy suggest breast cancer. I also measured ninety-five (95) samples from putatively healthy women. Twenty eight (28) of these samples are older women and the remainder are from blood donors. The blood donor cohort is significantly younger and consists, presumably, of mainly pre-menopausal women.

Normally, to measure five biomarkers in duplicate at 100 microliter per marker, I would need about 1.0 ml. I implemented an appropriate dilution scheme in which the biomarkers with higher abundance are measured in diluted samples. I set the dilution scheme so that all cytokines are measurable in all samples. This is possible only because of the superior sensitivity of Super-ELISA. I demonstrated the excellent sensitivity and specificity of my assay. The use of supersensitive assays (Super-ELISA, IA/MPD) and sophisticated methods of statistical analysis permitted excellent sensitivity and specificity of detection of breast cancer (BC) in the studied cohorts. I achieved better than 95% sensitivity and specificity (see Table 5).

TABLE 5

Breast Cancer Identification

|  | NT BC | Healthy women |
|---|---|---|
| No. of samples | 159 | 95 |
| Properly identified | 157 (98.1%) | 90 (94.7%) |
| Uncertain | 3 (1.9%) | 5 (5.3%) |
| Falsely identified | 0 (0.0%) | 0 (0.0%) |

We calculated a synthetic score from the measurement of these five biomarkers. I demonstrated that after integrating over age, untreated breast cancer samples have a score close to +100 units whereas most healthy women samples have a score below −50 units (see FIG. 40). Overall, the use of a panel of biomarkers permits the detection of breast cancer in almost all (>98%) women for which cancer has been previously detected by mammography (P-BC cohort). Actually, for the cohort in which the malignant tumor was detected during biopsy (C-BC cohort), I achieved 99% sensitivity. Almost all (ca. 95%) healthy women were properly identified.

In the evaluation of relevant diagnostic value, the FDA utilizes ROC curves to evaluate the efficacy of the test procedure in question. Typically, ROC curves at 80% are considered acceptable and at 90% are judged as excellent. Mammography (film and/or digital) is currently considered the diagnostic test of choice for breast cancer screening and has a charted ROC curve of approximately 80%. As presented in FIG. 41, we have demonstrated an ROC curve of almost 96% for our breast cancer test, which is far superior than any prior-art breast cancer detection method including both film and digital mammography.

It works only with supersensitive immunoassay: The presented data suggest that I achieved the landmark sensitivity and specificity in blood-based breast cancer detection. I need to elucidate if the main component of this success are:

appropriate selection of biomarkers;

ability to detect all low abundance biomarkers in all individuals;

innovative data analysis algorithms.

All the above elements need to be synergistically achieved to provide the ultrasensitive cancer detection. I documented, however, that the ultrasensitiity of my assays is crucial. For example, todays commercial assays for PSA have the limit of detection (LOD) of about 10 pg/ml. I documented that out of a cohort of 95 healthy women (HW-cohort), only 5 women are detectable with LOD(PSA)=10 pg/ml, 8 with LOD(PSA)=5 pg/ml and only 29 with LOD(PSA)=1 pg/ml. I achieved the LOD(PSA)=0.05 pg/ml, which permits reliable quantitation of the level of PSA in sera of all women in HW cohort. Similarly, for all cytokines, the current LODs permit detection of only a small fraction of women in HW cohort. My assays permit to quantitate all cytokines and AFS in all sera. Taking this into consideration, I evaluated the breast cancer detection sensitivity and specificity when using ELISA. The data are shown in Table 6 and shows the crucial importance of high analytical sensitivity.

TABLE 6

| | Super-ELISA | | ELISA | |
|---|---|---|---|---|
| | NT BC | Healthy women | NT BC | Healthy women |
| No. of samples | 159 | 95 | 159 | 95 |
| Properly identified | 157 (98.1%) | 90 (94.7%) | 151 (94.6%) | 83 (87.4%) |
| Uncertain | 2 (1.9%) | 5 (5.3%) | 8 (5.1%) | 11 (11.6%) |
| Falsely identified | 0 (0.0%) | 0 (0.0%) | 0 (0.0%) | 1 (1.0%) |

Breast Cancer Identification

We can observe, that the sensitivity (number of uncertain/false negatives) is only modestly influences when the assay analytical sensitivity is decreased. However, the specificity (number of uncertains/false positives) is much diminished.

EXAMPLE 2

Applications of Supersensitive Diagnostics Proteomics in Detection of Prostate Cancer Prostate cancer is the most common cancer of men in the USA and is second to lung cancer as a cause of death in men. The American Cancer Society estimates that approximately 190,000 to 200,000 new cases of prostate cancer will be diagnosed each year and that approximately 30,200 men will have died of the disease in 2002. Once prostate cancer is advanced and becomes hormone refractory there is no effective therapy. There is currently no known effective way to prevent prostate cancer. Thus, early detection with local treatment provides the best chance to reduce the morbidity and mortality of prostate cancer. Five million diagnostic tests in the USA and ten million worldwide are performed per year. There are 250 thousand prostatectomies in the USA every year. About 20% of men with removed prostate die due to metastasis.

Early stage prostate cancer is detected by a digital rectal exam and by measurement of blood levels of Prostate Specific Antigen (PSA). Introduction of the PSA test in the late 1980's detected many otherwise unapparent tumors. Since PSA in blood is produced by both normal prostate and by prostate tumors, reliance on high PSA levels alone for diagnosis leads to many false positives. Refinements to the PSA method have been sought to improve the discrimination of the technique and thus eliminate unneeded biopsies. The most successful refinement has been to use the ratio of free to bound PSA.

Early prostate cancer is asymptomatic and metastasis to lung, bone, lymph nodes and liver are common. Reference ranges for PSA by age have been established, i.e. from 2.5 to 6.5 ng/ml for ages 40-49 to 70-79, respectively. One-time measurements are not as descriptive as successive measurements over time, with tests at least once a year and more often when a higher level of PSA is detected or familial occurrence indicated. The change in serum PSA concentration over time is important. A PSA velocity of 0.06 ng/ml per month is seen as abnormal. These types of tests require a reproducibility of quantitation (LOQ) of a few pg/ml, which is rarely achieved with current tests. More sensitive and reproducible PSA assays are clearly needed.

Prostrate cancer recurrence and therapy monitoring: The rate of local recurrence of prostate cancer following a radical prostatectomy has been estimated at 15 to 20 percent. It is as high as 30% following external beam therapy. Today the recurrence of prostate cancer is detectable only a few years after operation. Current methods of detection are not sensitive enough to elucidate the existence of a sub-set of patients with much faster recurrences, say a few months. The classical indicator is a PSA level of more than 0.4 ng/ml for patients with a radical prostatectomy. However, it is recognized that a single measurement of the PSA level is not a reliable indicator. There are a number of indicators of recurrence, mostly looking for changes in the PSA level. Thus, one needs a new generation of PSA assays, which will be both more sensitive (better than pg/ml) and more reliable. A rising PSA level may indicate that the cancer has recurred locally, e.g. in the bed of the prostate, the surrounding fat tissue or the bladder wall. It may also indicate that the cancer has spread to other parts of the body. My super-sensitive PSA immunoassay is about 100-fold more sensitive than currently available assays and may detect the sub-pg/(ml*month) rise in level of PSA. It will be a superior tool in therapy monitoring and detection of early post-prostatectomy metastasis.

The use of prostate specific antigen (PSA) permits early detection of prostate cancer. The sensitivity is reasonable (>80%) but specificity is quite bad. About 60% of patients with the cut-off level of PSA (4 ng/ml) were documented by biopsy to have either benign prostate hyperplesia (BPH) or prostatitis. Thus, reliable differentiation between prostate cancer and BPH/prostatitis is an important challenge. Another important challenge is detection of cases in which patients after radical prostatectomy develop metastasis, which is often lethal. I demonstrated that by measuring both PSA and a plurality of cytokines and angiogenesis factors (IL-8, VEGF) I can reliably differentiate between different prostate diseases. The data are presented in Table 7. In FIG. 42, I present excellent identification using the appropriate synthetic score marker.

TABLE 7

Identification of prostate cancer versus PBH and prostatitis.

| | Disease | | |
|---|---|---|---|
| | Prostate Cancer | BPH | Prostatitis |
| No. samples | 17 | 60 | 21 |
| Properly identified | 17/17 (100%) | 59/60 (98%) | 21/21 (100%) |
| Uncertain | 0/17 (0%) | 1/60 (2%) | 0/21 (0%) |
| Falsely identified | 0/17 (0%) | 0/60 (0%) | 0/21 (0%) |

EXAMPLE 3

Correlating Level of Cytokine and Leukemia

The IA/MPD permits better sensitivity in quantifying a plurality of cytokines; its ability to accurately measure trace amounts of cytokines potentially could change my understanding on how subtle changes in cytokine concentrations could alter an immune response to cancer. I obtained a series of important results concerning the relationship between the levels of IL-1$_{beta}$, IL-6 and IL-10 with the prognosis of acute myelogenous leukemia (AML) patients. In this application, ELISA is clearly not sensitive enough. The results for IL-1$_{beta}$ are striking; about 70% of the 30 control samples show clearly measurable, though very low (<0.2 pg/ml) level. However, in all but three AML patients, the level of IL-1$_{beta}$ is clearly suppressed and cannot be measured even with IA/MPD. The samples were measured blind and in duplicate. These preliminary data strongly suggest that IL-1$_{beta}$ may become an important cancer marker. I measured about 60 samples, including 30 from AML patients. My data suggest that it is necessary to further improve the IA/MPD to a 1 fg/ml level.

In AML patients the levels of IL-1$_{beta}$ in blast cells are increased, but the serum levels are drastically decreased. As the levels of IL-1$_{beta}$ in blasts are a factor 5-10 higher and in serum is about 10 fold lower, I observe the factor fifty secretory modulation. Only large changes in level of post-translational modification can explain this result. These results strongly suggest the reduced activity of Caspase-1, which cleaves pro-IL-1$_{beta}$ and pro-IL-18 into their mature forms. Thus, immature IL-1$_{beta}$ is not secreted, but is retained within the cells. This remarkable result may illuminate an important problem of immunoregulation via caspases by providing a connection to the molecular biology of apoptosis. My studies of AML patients documented the first example of down-regulation of an interleukin in the case of cancer.

EXAMPLE 4

Early detection of Alzheimer Disease

Alzheimer's disease (AD) is a major public health problem. It is the fourth leading cause of death in the U.S., affecting over 2.5 million individuals. There is neither a definitive test nor therapy for this disease, though recently a plurality of drugs showed promise in clinical tests. However, increasing understanding of role of tau and beta-amyloid proteins offers a new opportunity for developing a diagnostic test for AD.

Current tests for Alzheimer are mostly behavioral, i.e. can detect the AD only in late, symptomatic phase. It is expected that the initial stages of disease leading to mild cognitive impairment (MCI) appears at least 10 to 20 years before the AD symptoms appear. Recently, treatments had been developed which slow down the transition from MCI to AD. Thus, it is important to develop the low cost molecular diagnostics for MCI. Currently, some diagnostic tests for tau protein and beta amyloid are in initial evaluation but they use cerebrospinal fluid. This is invasive and rather costly procedure that requires a short hospitalization after performance. The blood based assay for biomarkers of MCI would permit low cost screening. It is estimated, that such low cost ($20-50 per assay) testing should be performed on all persons 50-60 years old. Thus, the blood based testing for initial stages of AD may be a multi-billion market, wherein currently there is no competition.

Proprietary, "Correlation" Based Software for Analysis of Biomarkers Patterns in Oncology We expected that analysis of the data obtained using my super-sensitive methods of diagnostic proteomics would be possible using existing methods of biostatistics. My data shows that the distributions of almost all biomarkers are highly age-dependent and strongly non-Gaussian. Thus, existing packages of biostatistical software cannot be used. I documented that the 2D correlations between biomarkers have a much higher predictive power than the distributions of any and each biomarker analyzed separately. I had to develop a suite of programs to implement this new type of biostatistical analysis. This suite of programs contains both the data input, calculations, and sophisticated presentation software using wavelet and 3D modeling to facilitate the understanding of the obtained data sets. These programs may have many applications when any methods of immunodiagnostics and diagnostics proteomics are used. I expect that such a coordinated package of programs may be an important element of commercialization.

To achieve the higher than 90% predictive power, the proposed method tries to use all information contained in the set of measurements. Traditionally, a particular measurement is compared with average value for a statistically meaningful cohort ("cut-off assays"). In more modern assays, the distributions of healthy and diseased patients are compared one by one. The method I used utilizes the correlation between biomarkers to improve the assay's reliability. For example, with five biomarkers used in my breast cancer diagnostics, I have ten 2D correlation functions. With 6 biomarkers used in prostate cancer detection I have 15 correlation functions.

To enable user-friendly use of these innovative techniques, I developed a proprietary software package, using code in Delphi and C++. It includes the subroutines for data input, calculations, statistical analysis and visual presentation of results.

The preferred data analysis method using two biomarker correlations: In my blood-based test, I measured five biomarkers leading to two generalized 5D ellipsoids. Differentiation is possible if the overlap of these two different ellipsoids is small. However, such a presentation is not intuitive—I cannot visualize 5D objects. Thus, I selected a particular method of analysis in which I study the projections of these 5D object on separate 2D planes. There are ten such projections. This provides a healthy redundancy that makes my analysis more robust. I found that a serial presentation of 2D correlations provides a good visualization of which biomarkers are important. I performed clustering analysis of ten two variable correlation functions, each presenting a two dimensional distribution.

Each of the ten 2D correlation graphs can be treated as an independent assay. However, they are not "cut-off value" assays—both very low and very high values may be a sign of breast cancer. A good example of a 2D-biomarker analysis is the correlation of IL-8 with VEGF. The plane is divided into areas where there are mainly breast cancer (BC) samples or mainly healthy women (HW) samples. However, for other combinations of biomarkers, there are also "uncertainty zones", where the BC is intermixed with HW. In the following, such Regions of Interest (ROI) are denoted {+} for mostly BC, {?} for uncertain and {−} for mostly HW.

The predictive power of each of these ten 2D planes is similar to that of a "classical" assay with a sensitivity of >50%. The specificity is defined as the probability that healthy women are correctly recognized in the training set. It is between 50 to 90%, depending on the correlation pair. However, I also observe cases where the predictive power is significantly lower e.g. PSA vs. TNF$_{alpha}$.

Such a set of data is strongly synergistic, presenting different aspects of systemic response to cancer. This synergy can be used to further diminish the number of false positives and false negatives. I developed a new method using a synthetic score based on an appropriate majority rule. For a given patient, the score is increased by 1 when it belongs to {+} region, is left unchanged if it belongs to {?} region and is diminished by 1 when it belongs to {−} region. In each case, the scores are normalized to between −100% and +100%. For positive scores, I present the score as a ratio of actual score to maximum positive score. Negative scores are presented as a percent of the lowest negative score. Notice that almost all BC samples are on the positive side of score-graph and the average score is about 95% The fraction of BC samples with score+100 is about 45%.

The comparison of different algorithms: The following will compare the different classes of algorithms developed for studies of the cancer detection using panels of immunoassays using the case of the breast cancer diagnostics as described above.

Using my supersensitive methods, I measured the non-biased distribution of five biomarkers (PSA, $TNF_{alpha}$, IL-6, IL-8, VEGF). The superior quality of my data permits the use of innovative methods of data mining. Because I are not in a "garbage in, garbage out" situation, better and more predictive algorithms can be used. However, the data analysis has to take into consideration that:

The observed distributions are highly not Gaussian;

There is a very large, up to five logs, dynamic range for some of the biomarkers;

There is a very strong age dependence of the level of the biomarkers;

The age dependence is different for healthy women and women with breast cancer.

Not only the average value, but also the distribution of biomarkers levels, is age dependent.

This leads to a considerable complication because the majority of methods of bioinformatics and classical statistics assume a Gaussian distribution. In the following, I document that an innovative way of handling these rich sets of data permits excellent diagnostics. My method can be properly understood only by comparing the results of calculations using a ladder of algorithms with increasing sophistication. Two classes of these algorithms are known and use either the average values (Class I) or actual distributions of the values (Class II) for a plurality of biomarkers. These algorithms lead to sensitivities and specificities of about 70-80%, depending on details of implementation. I developed new classes of algorithms (Class III and IV). Using these algorithms, both the sensitivity and specificity is excellent (>90%).

It is convenient to divide the different algorithms into the following categories:

Algorithms using only average values of biomarkers;

Algorithms using the distributions of biomarkers (not accounting for age dependence);

Algorithms using 2D correlations of biomarkers (age dependence accounted for);

Algorithms using the 2D correlations of the derived functions of biomarkers.

Each of these classes of algorithms can be tuned to provide the most reliable diagnostics. However, such "tuning" leads to only a few percent improvement in the test's performance. The main difference is between particular classes. Briefly, the Class I and II algorithms do not use the correlations between different biomarkers, and lead to a relatively low sensitivity and specificity. Class III and IV lead to a considerable improvement. The Class III algorithms bring increased specificity by taking in account age variation. The Class II algorithms give excellent sensitivity and specificity even though the BC and HW cohorts consist of women with significant differences in age distribution. The algorithms in Class IV lead to further improvement in predictive power for older women when 2D correlations are used. Note that algorithms in Class III and IV take explicitly in consideration the strong age dependence and non-Gaussian distribution of the studied biomarkers. The overall view of predictive power of these six algorithms is provided in Table 8.

TABLE 8

Breast Cancer Identification using Class III and IV algorithms.

|  | NT-BC women | Healthy women |
|---|---|---|
| No. of samples | 159 | 95 |
| Class III algorithm |  |  |
| Properly identified | 151/159 (95.0%) | 92/95 (96.8%) |
| Uncertain | 7/159 (4.4%) | 2/95 (2.1%) |
| False identified | 1/159 (0.6%) | 1/95 (1.1%) |
| Class IV algorithm |  |  |
| Properly identified | 159/159 (100%) | 88/95 (92.6%) |
| Uncertain | 0 (0.0%) | 6/95 (6.3%) |
| False identified | 0 (0.0%) | 1/95 (1.1%) |

It can be seen that both algorithms give excellent sensitivity and specificity of better than 90%. Furthermore, the results are consistant between algorithms. Actually, Class III algorithm seems to have slightly better specificity and Class IV algorithm better sensitivity. Thus, two classes of algorithms are synergistsic and measurements for each serum sample should be evaluated using both algorithms.

The evaluation of the new algorithm using data sets from academia: My studies show that this method, based on detection of very low abundance proteins works, well in detection of breast cancer, prostate cancer and melanoma. I evaluated it using the data from IA/MPD, Super-ELISA and Luminex device. In collaboration with the group of Dr. A. Lokshin, I performed a study for the melanoma. I used the Luminex-based measurement of over 70 biomarkers performed using three cohorts: healthy individuals (n=44), pre-therapy melonoma patients (n=179) and post therapy melanoma patients (n=172). The first observation is that for a number of important biomarkers, e.g. $L-1_{beta}$, IL-6, IL-2, $TNF_{alpha}$ the Luminex system can detect biomarkers in less than 20% of healthy patients and less than 50% of melanoma patients. Also, a large number of outlayers is observed.

I compared the averages over two cohorts for the aforementioned about 70 biomarkers. The majority of (90%) of biomarkers have a very low predictive power when only averages are compared. Only seven biomarkers, all low abundance proteins, have a high predictive power. These are IL-6, IL-8, $TNF_{alpha}$, VEGF, $MP1_{alpha}$, $MP1_{beta}$ and MPA. I analyzed the distributions for these variables and demonstrated that IL-8 is the best single biomarker, with about 60% predictive power. Using classical methods of biostatistics and all 70 biomarkers, the detection sensitivity is at about 75%. Using my proprietary correlation-based method I achieved 95% sensitivity and specificity using only seven biomarkers. I expect that when a method of detection more sensitive than Luminex detection method is used, e.g. Super-ELISA or RGIA, the sensitivity and specificity can be further improved. The important point is that proteins with abundance above 50 pg/ml do not contribute significantly to the assay's predictive power. On the other hand, a few selected low abundance proteins provide reliable assay.

The need for user-friendly procedures requires the use of "expert software" which is currently not available commercially. Thus, I had to develop a considerable amount of proprietary software, which implements the innovative methods of proteomics data analysis. I tested this software using data obtained with my supersensitive methods (IA/MPD, Super-ELISA and P-chip/MPD). I tested the algorithms using data from high throughput but much lower sensitivity methods available commercially from Luminex Iic. I demonstrated that better than 90% sensitivity and sensitivity using my software, whereas the previous analysis achieved about 20% lower predictive power. Thus, my software provide a considerable advantage over the biostatistical methods used previously.

Comments about the robustness of the proposed assay: There are several important considerations when evaluating the panel of assays used for identification of cancer. The main challenge is to achieve a specificity better than 90%, i.e. to optimize the panel power in the rejection of false positives. I need to understand:

Dependence of the specificity of the proposed panel of assays on the sensitivity of each assay for a given biomarker;

Dependence of the specificity on the method of analysis;

Dependence of specificity on the selected biomarkers.

As mentioned, the assay sensitivity is crucial. For PSA and $TNF_{alpha}$, with typical, commercially available ELISA assays, I observe measurable values for no more than 20% of samples. However, even the loss of sensitivity by a factor of two will mean that the panel leads to higher number of "uncertain" outcomes between both HW and BC cohorts.

The use of optimized assay analysis is crucial. First, appropriate rejection of outliers needs to be implemented and appropriate age dependent averages should be reliably measured for all age-dependent biomarkers. Second, the use of 2D correlations leads to better specificity and to a more robust panel because it better accounts for 10-20% of outliers. Third, the F/G function method seems promising and provides well defined, robust identification of HW and BC cohorts for older women. The use of derived variables leads to both better understanding of immune/angiogenic properties of BC cohort and to better cohort delineation for older women. Overall, the use of optimal data analysis is crucial, mainly due to the strongly non-Gaussian character of distributions observed for particular biomarkers in BC cohorts.

The predictive power of different biomarkers in the discussed panel: Not all 2D correlation functions have the same predictive power. The predictive power is herein defined as the probability of rejecting a given HW sample based on its position on particular 2D correlation graph. Table 9 provides the contribution of a given 2D correlation function to the sensitivity, i.e. probability that a given sample is identified as belonging to NT-BC cohort.

TABLE 9

| | Predictive Power of 2D correlations | |
|---|---|---|
| Low | 50%-60% | PSA/TNF; PSA/IL-6, TNF/IL-6 |
| High | 60%-80% | PSA/IL-8, TNF/IL-8, TNF/VEGF, IL-8/VEGF |
| Very High | >80% | PSA/VEGF, IL-6/IL-8, IL-6/VEGF |

How many biomarkers one needs: Reducing the number of biomarkers measured may lead to operational and economic advantages. My analysis of 254 samples shows that measurement of all five biomarkers seems necessary for obtaining better than 90% specificity of the breast cancer assay. This aspect is discussed in the following in the framework of analysis using the direct variables.

Our set of data suggests that the biomarker with the lowest predictive power is $TNF_{alpha}$. When the 2D correlations between the biomarkers are used and all measurements of $TNF_{alpha}$ are rejected, there is a few percent reduction in the specificity of panel. When using the direct variables, neglecting the IL-6 or IL-8 or VEGF leads to a substantial (15-20%) decrease in specificity, i.e. the number of false positives increases considerably. When derived variables are used, panel performances are better stabilized even when using only four rejecting biomarkers. However, when IL-6 or VEGF are not accounted for, the number of false positives increases and a new region of interest (scores 0 to +50) becomes important, wherein a ROI of "uncertains" is now applied to both HW and BC cohorts. The biomarkers with the highest predictive power are two angiogenesis factors, IL-8 and VEGF. Thus, it may be important to add to my assay another angiogenesis factor, e.g. FGF1. The loss of predictive power when one of the biomarkers is omitted is illustrated in the Table 10.

TABLE 10

| Breast Cancer Identification using less than five biomarkers. | | | |
|---|---|---|---|
| | Properly identified | Uncertain | False identified |
| All biomarkers | | | |
| NT-BC | 157/159 = 98.7% | 2/159 = 1.3% | 0/159 = 0.0% |
| HW | 92/95 = 96.8% | 3/95 = 3.2% | 0/95 = 0.0% |
| $TNF_{alpha}$ removed | | | |
| NT-BC | 151/159 = 95.0% | 4/159 = 3.1% | 3/159 = 1.9% |
| HW | 90/95 = 94.7% | 2/95 = 2.1% | 3/95 = 3.2% |
| IL-6 removed | | | |
| NT-BC | 138/159 = 86.8% | 13/159 = 8.2% | 8/159 = 5.0% |
| HW | 88/95 = 92.6% | 2/95 = 2.1% | 5/95 = 5.3% |
| IL-8 removed | | | |
| NT-BC | 142/159 = 89.3% | 9/159 = 5.7% | 8/159 = 5.0% |
| HW | 86/95 = 90.5% | 1/95 = 1.1% | 8/95 = 8.4% |
| VEGF removed | | | |
| NT-BC | 146/159 = 91.8% | 6/159 = 3.8% | 7/159 = 4.4% |
| HW | 88/95 = 92.6% | 0/95 = 0.0% | 7/95 = 7.4% |

We note that PSA is the unique biomarker which differentiates the response to breast cancer vs. other cancers, i.e. it cannot be removed from the panel. $TNF_{alpha}$ could be removed but then the important aspect of assymetry of immune response would be lost. The rejection of any of the other biomarker(s) leads to a significant loss of sensitivity and specificity and should be retained. Note that rejection of IL-6 and IL-8 influences the number of samples from HW cohort which are uncertain or falsely identified, i.e. influence mostly specificity. The removal of VEGF from the panel influences mostly the number of uncertain samples in BC cohort, i.e. influences the sensitivity.

It will be readily apparent to those skilled in this art, from the detailed description and drawings, that which is shown and described is the preferred embodiments of the new invention and the best mode contemplated for carrying out the invention. The invention, therefore, is capable of other and different embodiments, and without departing from the invention, the description and drawings are illustrative and not restrictive.

What is claimed:

1. A super-sensitive sandwich immunoassay which can quantitate proteins with a detection level at less than 100 fg/ml by reducing biological background interference in the specimen to be tested comprising the steps of:
    (a) coating a testing substrate with an $Abs_{(capture)}$ solution and allowing incubation and bonding between the testing substrate and the $Abs_{(capture)}$ solution;
    (b) super stringent washing the testing substrate;
    (c) treating the testing substrate with a blocking reagent;
    (d) super stringent washing the testing substrate;

(e) depositing a sample of physiologic fluid on the testing substrate;
(f) super stringent washing the testing substrate;
(g) applying an $Abs_{(labeling)}$ solution onto the testing substrate and allowing incubation;
(h) super stringent washing the testing substrate;
(i) applying a streptavidin based reagent onto the testing substrate;
(j) super stringent washing the testing substrate; and
(k) measuring and generating a signal representative of ultra-low amounts of labeled antibodies at detection levels less than 100 fg/ml,
wherein the level of protein is ascertained using one or more of the following:
  a. multi photon detection (MPD) instrumentation which can quantitate proteins with a limit of detection of less than 10 fg/mg, using $^{125}I$ radiolabels;
  b. optical colorimeter readers having a signal capable of quantitating proteins at a limit of detection less than 50 fg/ml;
wherein super-sensitivity is obtained by use of super-stringent washing wherein the protein detection ability is diminished by a factor greater than 3; and
wherein the supersensitive washing is obtained using one or more of the following procedures:
  a. application of ultrasound;
  b. application of shock waves;
  c. movement of small magnetic actuator, wherein the rotational movement of the said magnetic actuator is induced by a strong external source of magnetic field;
  d. application of turbulent washing liquid having a temperature higher than room temperature
  e. application of turbulent washing liquid pH significantly different than pH=7 for at least 10 minutes; and
  f. washing using an application of a "slow-roll" technique.

2. A super-sensitive sandwich immunoassay according to claim 1, wherein the super-stringent washing is obtained by combination of at least two methods as described therein.

3. A super-sensitive sandwich immunoassay according to claim 1, wherein the super-sensitive immunoassay is performed in 96- or 384- well microtiter plates and capture antibodies are added in considerable excess, incubated for more than 1 hour, and then super-stringently washed.

4. A super-sensitive sandwich immunoassay according to claim 3, wherein cross-talk between capture antibodies and labeling antibodies is diminished by selecting antibodies which have a low interaction probability and wherein said capture antibodies are provided at less than 1 microgram/well.

5. A super-sensitive sandwich immunoassay to claim 1, wherein said immunoassay includes microtiter plates which are blocked with a blocking liquid consisting of one or more of the following products that have been purified by removing biotinylated proteins:
  a) caseine, caseine byproducts or caseine chemical derivatives;
  b) plant products imitating milk, including soy milk;
  c) fine granulated graphite or other simple organic product.

6. A super-sensitive sandwich immunoassay according to claim 5, wherein said microtiter plates are blocked with a graphite powder selected to contain a large spectrum of graphite granules, wherein said large spectrum of graphite granules is obtained by the mixing at least two commercially available graphite based powders wherein graphite granules with a diameter larger than approximately 50 microns are removed by filtration.

7. A super-sensitive sandwich immunoassay according to claim 6, wherein said graphite powder is selected to consist mainly of granules having a diameter smaller than approximately 5 microns, and wherein coagulation of said graphite powder is reduced by placing said graphite powder in a water based liquid with additives which diminish the coagulation of graphite granules or wherein the said graphite powder is charged negatively.

8. A super-sensitive sandwich immunoassay according to claim 1, that includes the step of incubation of labeling antibodies in an assay buffer with pH substantially different than PH=7.

9. A super-sensitive sandwich immunoassay which can quantitate proteins with detection level at less than 100 fg/ml by reducing biological background interference in the specimen to be tested comprising the steps of:
  (a) coating a testing substrate with an $Abs_{(capture)}$ solution and allowing incubation and bonding between the testing substrate and the $Abs_{(capture)}$ solution;
  (b) super stringent washing the testing substrate;
  (c) treating the testing substrate with a blocking reagent;
  (d) super stringent washing the testing substrate;
  (e) depositing a sample of physiologic fluid on the testing substrate;
  (f) super stringent washing the testing substrate;
  (g) applying an $Abs_{(labeling)}$ solution onto the testing substrate and allowing incubation;
  (h) super stringent washing the testing substrate;
  (i) applying a streptavidin based reagent onto the testing substrate;
  (j) super stringent washing the testing substrate; and
  (k) measuring and generating a signal representative of ultra-low amounts of labeled antibodies at detection levels less than 100 fg/ml, wherein super-sensitive assay incorporates a buffer having greater than 10% per mass component of fraction IV human serum.

10. A super-sensitive sandwich immunoassay which can quantitate proteins with a detection level at less than 100 fg/ml by reducing biological background interference the specimen to be tested comprising the steps of:
  (a) coating a testing substrate with an $Abs_{(capture)}$ solution and allowing incubation and bonding between the testing substrate and the $Abs_{(capture)}$ solution;
  (b) super stringent washing the testing substrate;
  (c) treating the testing substrate with a blocking reagent;
  (d) super stringent washing the testing substrate;
  (e) depositing a sample of physiologic fluid on the testing substrate;
  (f) super stringent washing the testing substrate;
  (g) applying an $Abs_{(labeling)}$ solution onto the testing substrate and allowing incubation;
  (h) super stringent washing the testing substrate;
  (i) applying a streptavidin based reagent onto the testing substrate;
  (j) super stringent washing the testing substrate; and
  (k) measuring and generating a signal representative of ultra-low amounts of labeled antibodies at detection levels less than 100 fg/ml, wherein the super-sensitive assay incorporates a buffer having greater than 10% per mass component of bird, reptile or fish serum.

11. A super-sensitive sandwich immunoassay which can quantitate proteins with a detection level at less than 100 fg/ml by reducing biological background interference in the specimen to be tested comprising the steps of:
  (a) coating a testing substrate with an $Abs_{(capture)}$ solution and allowing incubation and bonding between the testing substrate and the $Abs_{(capture)}$ solution;

(b) super stringent washing the testing substrate;
(c) treating the testing substrate with a blocking reagent;
(d) super stringent washing the testing substrate;
(e) depositing a sample of physiologic fluid on the testing substrate;
(f) super stringent washing the testing substrate;
(g) applying an $Abs_{(labeling)}$ solution onto the testing substrate and allowing incubation;
(h) super stringent washing the testing substrate;
(i) applying a streptavidin based reagent onto the testing substrate;
(j) super stringent washing the testing substrate; and
(k) measuring and generating a signal representative of ultra-low amounts of labeled antibodies at detection levels less than 100 fg/ml, wherein the super-sensitive assay incorporates a buffer having greater than 10% per mass component of milk, milk byproducts or plant extracted proteins or soy byproducts.

12. A super-sensitive sandwich immunoassay which can quantitate proteins with a detection level at less than 100 fg/ml by reducing biological background interference in the specimen to be tested comprising the steps of:
(a) coating a testing substrate with an $Abs_{(capture)}$ solution and allowing incubation and bonding between the testing substrate and the $Abs_{(capture)}$ solution;
(b) super stringent washing the testing substrate;
(c) treating the testing substrate with a blocking reagent;
(d) super stringent washing the testing substrate;
(e) depositing a sample of physiologic fluid on the testing substrate;
(f) super stringent washing the testing substrate;
(g) applying an $Abs_{(labeling)}$ solution onto the testing substrate and allowing incubation;
(h) super stringent washing the testing substrate;
(i) applying a streptavidin based reagent onto the testing substrate;
(j) super stringent washing the testing substrate; and
(k) measuring and generating a signal representative of ultra-low amounts of labeled antibodies at detection levels less than 100 fg/ml, which includes the steps of labeling an antibody, incubating said antibody and performing a super-stringent wash to remove more than 50% of incubated labeled antibody, wherein super-stringent washing is performed according to one or more of the following procedures:
   a. application of ultrasound;
   b. application of shock waves;
   c. movement of small magnetic actuator, wherein the rotational movement of said magnetic actuator is induced by a strong external source of magnetic field;
   d. application of turbulent washing liquid having a temperature higher than room temperature
   e. application of turbulent washing liquid with pH significantly different than pH=7 for at least 10 minutes; and
   f. washing using an application of a "slow-roll" technique.

13. A super-sensitive sandwich immunoassay according to claim 12, wherein said labeled antibody is labeled with EC emitter, wherein said labeled antibody is derivatized with biotin, and wherein a reagent containing at least one streptavidin labeled moiety having an enzymatic or 125-I radioactive label is used to provide a measurable signal via binding to said biotinylated labeled antibody.

14. A super-sensitive sandwich immunoassay according to claim 13 wherein the said streptavidin is labeled with the enzymatic label horseradish peroxidase (HRP) and wherein the biological stickiness of streptavidin base reagent is diminished by:
   shortening of incubation time;
   use of optimal pH and/or temperature;
   super-stringent wash, wherein said super-stringent washing is implemented in accordance with one or more of the following procedures:
      a. application of ultrasound;
      b. application of shockwaves;
      c. movement of small magnetic actuator, wherein the rotational movement of said magnetic actuator is induced by a strong external source of magnetic field;
      d. application of turbulent washing liquid having a temperature higher than room temperature
      e. application of turbulent washing liquid with pH significantly different than pH=7 for at least 10 minutes; and
      f application of a "slow-roll" washing technique.

15. A super-sensitive sandwich immunoassay according to claim 14 wherein biological background due to stickiness of $^{125}$I-streptavidin is diminished by application of $^{125}$I-streptavidin with activity no larger than 10,000 dpm per well and wherein biological background is diminished by application of $^{125}$I-streptavidin for no longer than 5 minutes.

16. A super-sensitive sandwich immunoassay according to claim 13 wherein multiple iodination is obtained by modifying utilizing genetically engineered streptavidin having multiple additional thyrosines in the tetramer of streptavidin.

17. A super-sensitive sandwich immunoassay according to claim 16 wherein the genetically engineered steptavidin is streptavidin-HRP or streptavidin-polyHRP, and wherein biological background due to stickiness of streptavidin-HRP or streptavidin-polyHRP is diminished at least five fold by super-stringent washing.

18. A super-sensitive sandwich immunoassay according to claim 17, having a labeled steptavidin wherein said labeled steptavidin is streptavidin HRP(i) with 1<i<80, and the signal is obtained by change of color induced by HRP or polyHRP e; or streptavidin, streptavidin-HRP or streptavidin-polyHRP derivitized with appropriate fluorescent tag.

19. A super-sensitive sandwich immunoassay according to claim 13 wherein said streptavidin moiety is used in two steps signal amplification techniques of amplified immunoassay/multi photon detection (IA/MPD), amplified Super-ELISA or amplified reverse geometry immunoassay (RGIA).

20. A super-sensitive sandwich immunoassay according to claim 19 wherein biotinylated anti-HRP is used to bind to streptavidin-polyHRP which streptavidin-polyHRP is first subjected to a super-stringent wash, and then used to implement amplified Super-ELISA.

21. A super-sensitive sandwich immunoassay which can quantitate proteins with a detection level at less than 100 fg/ml by reducing biological background interference in the specimen to be tested comprising the steps of:
(a) coating a testing substrate with an $Abs_{(capture)}$ solution and allowing incubation and bonding between the testing substrate and the $Abs_{(capture)}$ solution;
(b) super stringent washing the testing substrate;
(c) treating the testing substrate with a blocking reagent;
(d) super stringent washing the testing substrate;
(e) depositing a sample of physiologic fluid on the testing substrate;
(f) super stringent washing the testing substrate;
(g) applying an $Abs_{(labeling)}$ solution onto the testing substrate and allowing incubation;
(h) super stringent washing the testing substrate;

(i) applying a streptavidin based reagent onto the testing substrate;

(j) super stringent washing the testing substrate; and (k) measuring and generating a signal representative of ultra-low amounts of labeled antibodies at detection levels less than 100 fg/ml, wherein said sandwich immunoassay is performed in 96-well microtiter plates having the volume of a biological sample to be placed in said plates increased above 300 microliter by multiloading or "slow- roll" technique and including a superstringent wash.

22. A super-sensitive sandwich immunoassay according to claim 21 wherein glass tubes tightly fitting the microtiter plate include glass tubes tightly fitting said plate which are used to implement "slow roll" movement and wherein the amount of biological sample is selected to provide at least 100 microliter of air in said glass tubes and wherein the rotational speed of "slow roll" is below 20 rotations per minute and the time of rotation in "slow roll" technique is at least 10 minutes.

23. A super-sensitive sandwich immunoassay according to claim 21, wherein the sandwich immunoassay is performed with capture antibodies coated on a substrate surface different than the microtiter plates, whereby the volume of said biological sample may be larger than 200 microliters by us of a granulated substrate.

24. A super-sensitive sandwich immnunoassay according to claim 23 wherein said substrate surface is one of the group consisting of diverse plastics not including polypropylene; diverse glasses; diverse magnetic materials; and diverse metals.

25. A super-sensitive sandwich immunoassay according to claim 23, wherein the sandwich immunoassay is performed using diverse glasses as a substitute surface and HRP or other enzymes are used as a label.

26. A super-sensitive sandwich immunoassay according to claim 23 wherein the granulated, substrate comprises microscopic or macroscopic beads.

* * * * *